US011648072B2

(12) United States Patent
Liao et al.

(10) Patent No.: US 11,648,072 B2
(45) Date of Patent: May 16, 2023

(54) SYSTEM AND METHOD FOR PATIENT-SIDE INSTRUMENT CONTROL

(71) Applicant: INTUITIVE SURGICAL OPERATIONS, INC., Sunnyvale, CA (US)

(72) Inventors: Hsien-Hsin Liao, Sunnyvale, CA (US); Brandon D. Itkowitz, San Jose, CA (US); Julie L. Berry, San Jose, CA (US); Pushkar Hingwe, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 212 days.

(21) Appl. No.: 17/065,483

(22) Filed: Oct. 7, 2020

(65) Prior Publication Data
US 2021/0015568 A1   Jan. 21, 2021

Related U.S. Application Data

(63) Continuation of application No. 15/580,629, filed as application No. PCT/US2016/036849 on Jun. 10, 2016, now Pat. No. 10,806,530.
(Continued)

(51) Int. Cl.
*A61B 34/35* (2016.01)
*A61B 34/30* (2016.01)
(Continued)

(52) U.S. Cl.
CPC .............. *A61B 34/35* (2016.02); *A61B 34/30* (2016.02); *A61B 34/70* (2016.02); *A61B 2090/064* (2016.02); *A61B 2090/066* (2016.02)

(58) Field of Classification Search
CPC ......... A61B 34/30; A61B 34/35; A61B 34/70; A61B 2090/066; A61B 2090/064
See application file for complete search history.

(56) References Cited

U.S. PATENT DOCUMENTS

| 6,788,018 B1 | 9/2004 | Blumenkranz |
| 8,388,556 B2 | 3/2013 | Wallace et al. |

(Continued)

FOREIGN PATENT DOCUMENTS

| EP | 2612616 A1 | 7/2013 |

OTHER PUBLICATIONS

Extended European Search Report for Application No. 16808354.1, dated Jan. 7, 2019, 9 pages.
(Continued)

*Primary Examiner* — Stephen Holwerda
(74) *Attorney, Agent, or Firm* — Artegis Law Group, LLP

(57) ABSTRACT

Systems and methods for instrument control include first and second actuators and a controller configured to command the first actuator to maintain a first degree of freedom (DOF) of an instrument at a first position; command the second actuator to maintain a second DOF of the instrument at a second position; detect, while the first actuator is maintaining the first DOF at the first position, a first manual actuation of the first actuator that exceeds a first threshold; detect, while the second actuator is maintaining the second DOF at the second position, a second manual actuation of the second actuator that does not exceed a second threshold; and in response to detecting that the first manual actuation exceeds the first threshold and the second manual actuation does not exceed the second threshold, terminate the command to the first actuator to maintain the first DOF at the first position.

20 Claims, 12 Drawing Sheets

Related U.S. Application Data

(60) Provisional application No. 62/173,856, filed on Jun. 10, 2015.

(51) Int. Cl.
 A61B 34/00 (2016.01)
 A61B 90/00 (2016.01)

(56) References Cited

U.S. PATENT DOCUMENTS

| | | | |
|---|---|---|---|
| 10,806,530 | B2 | 10/2020 | Liao et al. |
| 2002/0082612 | A1 | 6/2002 | Moll et al. |
| 2007/0013336 | A1* | 1/2007 | Nowlin .................. A61B 34/37 318/568.21 |
| 2007/0142823 | A1 | 6/2007 | Prisco et al. |
| 2008/0046122 | A1 | 2/2008 | Manzo et al. |
| 2009/0024142 | A1 | 1/2009 | Ruiz Morales |
| 2010/0137882 | A1 | 6/2010 | Quaid, III et al. |
| 2010/0168723 | A1* | 7/2010 | Suarez .................. A61B 90/50 606/1 |
| 2011/0082587 | A1 | 4/2011 | Ziaei et al. |
| 2014/0039517 | A1* | 2/2014 | Bowling .................. B25J 9/161 606/130 |
| 2014/0052154 | A1 | 2/2014 | Griffiths et al. |
| 2015/0051733 | A1 | 2/2015 | Nowlin et al. |
| 2015/0100066 | A1* | 4/2015 | Kostrzewski .......... A61B 34/30 606/130 |
| 2017/0172671 | A1 | 6/2017 | Miller et al. |

OTHER PUBLICATIONS

International Search Report and Written Opinion for Application No. PCT/US2016/036849, dated Sep. 12, 2016, 12 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEM AND METHOD FOR PATIENT-SIDE INSTRUMENT CONTROL

RELATED APPLICATION

This patent application is a continuation of U.S. patent application Ser. No. 15/580,629, filed on Dec. 7, 2017, which is a U.S. National Stage patent application of International Patent Application No. PCT/US2016/036849, filed on Jun. 10, 2016, the benefit of which is claimed, and claims priority to and the benefit of the filing date of U.S. Provisional Patent Application 62/173,856, entitled "SYSTEM AND METHOD FOR PATIENT-SIDE INSTRUMENT CONTROL" and filed Jun. 10, 2015, each of which is incorporated by reference herein in its entirety.

COPYRIGHT NOTICE

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

BACKGROUND

1. Field of Invention

The inventive aspects disclosed here relate generally to the operation of a teleoperated surgical system, and more specifically, to a control algorithm implemented on a teleoperated surgical system that enables manual control of a teleoperated surgical instrument from the patient side.

2. Art

A teleoperated surgical system including one or more computer-controlled motors can allow a medical person to remotely control a surgical instrument. Some teleoperated surgical systems include a surgeon's console housing one or more control inputs in communication with the one or more computer-controlled motors. The surgeon's console can additionally include a video display that is in communication with a camera located at a surgical site. The computer-controlled motors move in response to the medical person's control of the one or more control inputs while viewing the video display. The motions of the computer-controlled motors operate a surgical instrument coupled to the motors.

In some cases, it is desirable to provide a means of controlling said surgical instrument to someone other than the medical person seated a surgeon's console. One example of a situation in which this additional means of control is desirable is in an emergency situation. In an emergency situation, the medical person seated at the surgeon's console is not located immediately beside the patient undergoing surgical treatment. In such a situation, a medical person located beside the patient (i.e., located at the patient side) may be better able coordinate with other medical persons to quickly remedy the emergency situation.

Surgical instruments provided for use with a teleoperated surgical system generally include an end effector. The end effector is the business end of the surgical instrument that performs the tasks associated of a surgical procedure. Examples of various types of end effectors include forceps, graspers, scissors, needle drivers, and the like. Often, specific forceps and graspers are purposed specifically to securely grasp patient tissue, for example to enable retraction of tissue during a surgical procedure that would otherwise block a surgeon's view of other tissue of interest.

In certain cases, an emergency situation arises at a time when a surgical instrument on a teleoperated surgical system is securely grasping tissue. Sometimes remedying the emergency situation requires removal of the surgical instrument from the surgical field. In these cases, it is desirable to provide a medical person located at the patient side with a means to release the surgical instrument's grasp of patient tissue before the surgical instrument is removed, so as to not cause damage to grasped tissue and surrounding anatomy.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

In one aspect, an algorithm executed by a teleoperated surgical system enables a user to manually control a teleoperated surgical instrument from the patient side. The teleoperated surgical system includes a first teleoperated actuator configured to actuate a first mechanical degree of freedom of the surgical instrument and a second teleoperated actuator configured to actuate a second mechanical degree of freedom of the surgical instrument. While the first teleoperated actuator is being commanded to maintain its current position, an application of an external force that is in excess of a first force threshold is detected. Meanwhile, at the second teleoperated actuator, which is being commanded to maintain its current position, no application of external force that is in excess of a second force threshold is detected. Upon detecting these conditions, the command to the first teleoperated actuator to maintain its current position is terminated.

In another aspect, a medical device includes a control input and a manipulator including a first teleoperated actuator and a second teleoperated actuator. The instrument manipulator is configured to receive a surgical instrument. The first teleoperated actuator is configured to actuate a first mechanical degree of freedom of the surgical instrument and the second teleoperated actuator is configured to actuate a second degree of freedom of the surgical instrument. A controller of the medical device is configured to control movement of the surgical instrument in response to movement of the control input. The controller is further configured to detect, while the first teleoperated actuator is being commanded to maintain its current position, an application of an external force to the first teleoperated actuator that is in excess of a first force threshold. Additionally, the controller is configured to detect, while the a second teleoperated actuator being teleoperated to maintain its current position, no application of external force to the second teleoperated actuator that is in excess of a second force threshold. Upon detecting these conditions, the controller is configured to terminate the command to the first teleoperated actuator to maintain its current position.

DETAILED DESCRIPTION

Figure 1:
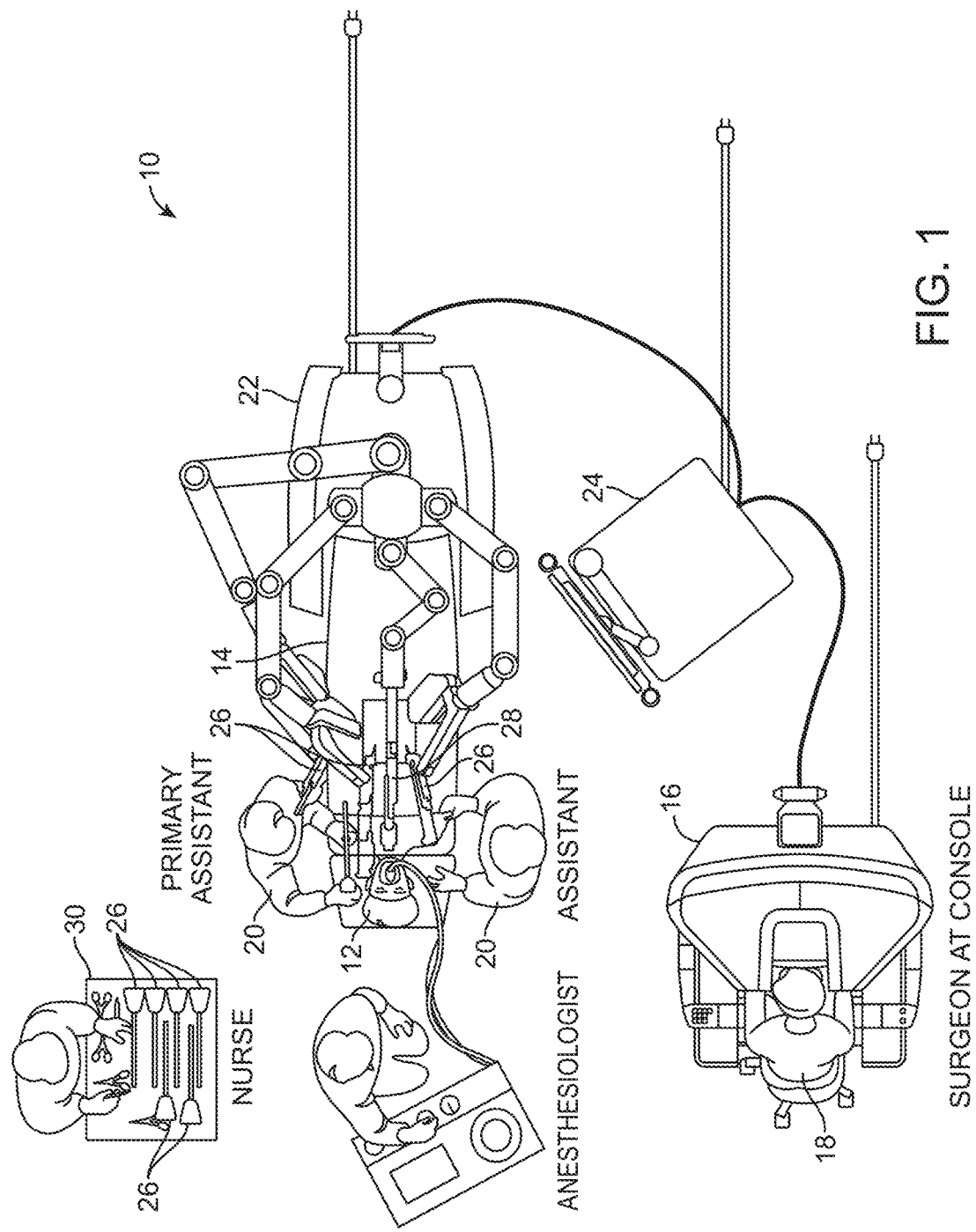
FIG. 1 is a plan view of a minimally invasive teleoperated surgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Aspects of the invention are described primarily in terms of an implementation using a da Vinci® surgical system (specifically, a Model IS4000, marketed as the da Vinci® Xi™ HD™ surgical system), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® surgical systems (e.g., the Model IS3000, commercialized as the da Vinci® Si™ HDTM surgical system; the Model IS2000, commercialized as the da Vinci® S™ HDTM surgical system) are merely exemplary and are not to be considered as limiting the scope of the inventive aspects disclosed herein.

As used here, the term "back-drive" shall describe a situation in which an external force applied to an output component is transmitted, either directly or through an intermediate mechanism, to an input component. The terms "input component" and "output component" are descriptive of the function served by a given component under normal operation. During normal operation, the direction of force transmission is typically from input component to output component. This force transmission from input component to output component can be described as forward-driving the mechanism. Back-driving, thus, is the opposite of forward-driving.

As an example, a surgical instrument that is used with a teleoperated surgical system can forward-driven in the following manner. The surgical instrument can include an input component and an output component. During normal operation of the surgical instrument, a force applied to the input component of the surgical instrument is transmitted by a transmission mechanism (e.g., gears, pulleys, pullwires, etc.) to an output component of the surgical instrument. The force applied to the instrument input can be applied by a teleoperated actuator of a teleoperated surgical system. In one example, the input component is a rotary input of the surgical instrument ("instrument input"), and the output component is component of a surgical instrument end effector such as movable jaw member. A mechanical force that is applied to the instrument input can be transmitted, e.g., by a pullwire, to move the movable jaw member. In another example, the input component is an instrument input, and the output component is a component of an orientable wrist coupled to the instrument input through one or more pullwires. During normal operation, a mechanical force that is applied to the instrument input is be transmitted through one or more pullwires to move the component of the orientable wrist.

In one aspect, one or more mechanical degrees of freedom of the surgical instrument described above can also be back-driven. As used here, back-driving is the opposite of forward-driving. In one example, an instrument input that is coupled to a movable jaw member by one or more pullwires can be back-driven by a force applied to the movable jaw member. When this back-driving takes place, the force applied to the movable jaw member is transmitted by the one or more pullwire to the instrument input. In one example, the instrument input is a rotary input of the surgical instrument, and the force applied to the movable jaw member rotates the instrument input relative to the rest of the surgical instrument. In one aspect, this surgical instrument is coupled to an instrument manipulator of a teleoperated surgical system, and the instrument input is mechanically coupled to a teleoperated instrument actuator. In this situation, the force applied to the movable jaw member can be further transmitted to the teleoperated actuator.

With reference to the surgical instrument described above, in one aspect, the movable jaw member and the instrument input that is coupled to the movable jaw member are both additionally coupled to a mechanical feature for manual actuation of the movable jaw member. In one case, this mechanical feature for manual actuation of the movable jaw member is configured to be kinematically downstream of the instrument input, and involves part of the transmission mechanism that couples the instrument input to the movable jaw. For example, the mechanical feature can be a lever that is mechanically coupled to one or more elements of the transmission mechanism. Accordingly, an external force applied to the lever is transmitted to the transmission mechanism, which in turn transmits this force to the movable jaw member. Alternatively, the mechanical feature can be a keying feature that is mechanically coupled to elements of the transmission mechanism. Accordingly, an external force applied to the keying feature can be transmitted to the transmission mechanism, which in turn transmits this force to the movable jaw member.

As discussed previously, in one aspect, this mechanical feature is coupled to the instrument input in addition to the movable jaw member. Accordingly, if an external force is applied to the mechanical feature, the transmission mechanism transmits this force to the instrument input in addition to the movable jaw member. This transmission of force from the mechanical feature to the instrument input is one example of back-driving the instrument input.

It is worth noting that not all mechanism that can be forward-driven are capable of being back-driven. One example of a mechanism that cannot be back-driven is a drive mechanism including a lead screw and a driven nut. The leadscrew is typically configured to permit only rotational motion (i.e., it is restrained from translating). Typically, this mechanism is forward-driven by rotating the leadscrew relative to the driven nut. The rotation of the leadscrew relative to the nut translates the nut along a longitudinal axis of the leadscrew. This mechanism, however, is generally incapable of being backdriven. Said another way, one cannot try translate the driven nut along the longitudinal axis of the leadscrew to cause a rotation of the leadscrew.

Minimally Invasive Teleoperated Surgical System

Referring now to the drawings, in which like reference numerals represent like parts throughout the several views, FIG. 1 is a plan view of a minimally invasive teleoperated surgical system 10, typically used for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes a patient-side cart 22 and an electronics cart 24. The patient-side cart 22 can manipulate at least one removably coupled instrument 26 through a minimally invasive incision in the body of the patient 12 while the surgeon 18 views the surgical site through the surgeon's console 16. An image of the surgical site can be obtained by an endoscope 28, such as a stereoscopic endoscope, which can be manipulated by the patient-side cart 22 to orient the endoscope 28. Computer processors located on the electronics cart 24 can be used to process the images of the surgical site for subsequent display to the surgeon 18 through the surgeon's console 16. The number of surgical instruments 26 used at one time will generally depend on the diagnostic or surgical procedure and the space constraints within the operating room among other factors. If it is necessary to change one or more of the instruments 26 being used during a procedure, an assistant 20 can remove the instrument 26 from the patient-side cart 22, and replace it with another instrument 26 from a tray 30 in the operating room.

Figure 2:
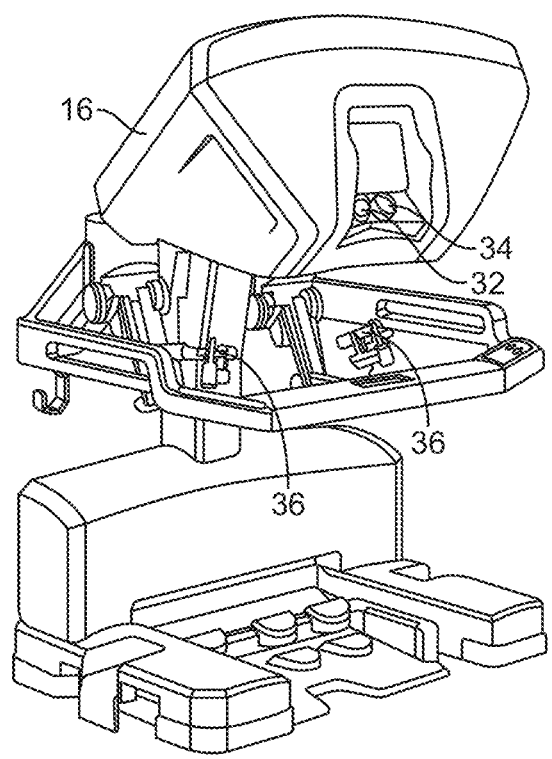
FIG. 2 is a perspective view of a surgeon's console.

FIG. 2 is a perspective view of the surgeon's console 16. The surgeon's console 16 includes a left eye display 32 and a right eye display 34 for presenting the surgeon 18 with a coordinated stereoscopic view of the surgical site that enables depth perception. The console 16 further includes one or more input control devices 36. One or more instruments installed for use on the patient-side cart 22 (shown in FIG. 1) move in response to surgeon 18's manipulation of the one or more input control devices 36. The input control devices 36 can provide the same mechanical degrees of freedom as their associated surgical instruments 26 (shown in FIG. 1) to provide the surgeon 18 with telepresence, or the perception that the input control devices 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the input control devices 36.

The surgeon's console 16 is usually located in the same room as the patient so that the surgeon can directly monitor the procedure, be physically present if necessary, and speak to a patient-side assistant directly rather than over the telephone or other communication medium. But, the surgeon can be located in a different room, a completely different building, or other remote location from the patient allowing for remote surgical procedures.

Figure 3:
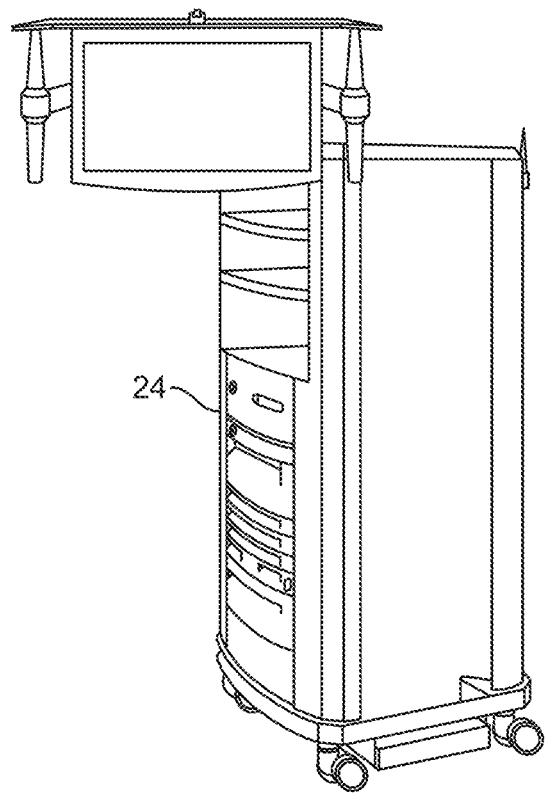
FIG. 3 is a perspective view of an electronics cart.

FIG. 3 is a perspective view of the electronics cart 24. The electronics cart 24 can be coupled with the endoscope 28 and includes a processor to process captured images for subsequent display, such as to a surgeon on the surgeon's console, or on another suitable display located locally and/or remotely. For example, if a stereoscopic endoscope is used, a processor on electronics cart 24 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Optionally, equipment in electronics cart may be integrated into the surgeon's console or the patient-side cart, or it may be distributed in various other locations in the operating room.

Figure 4:
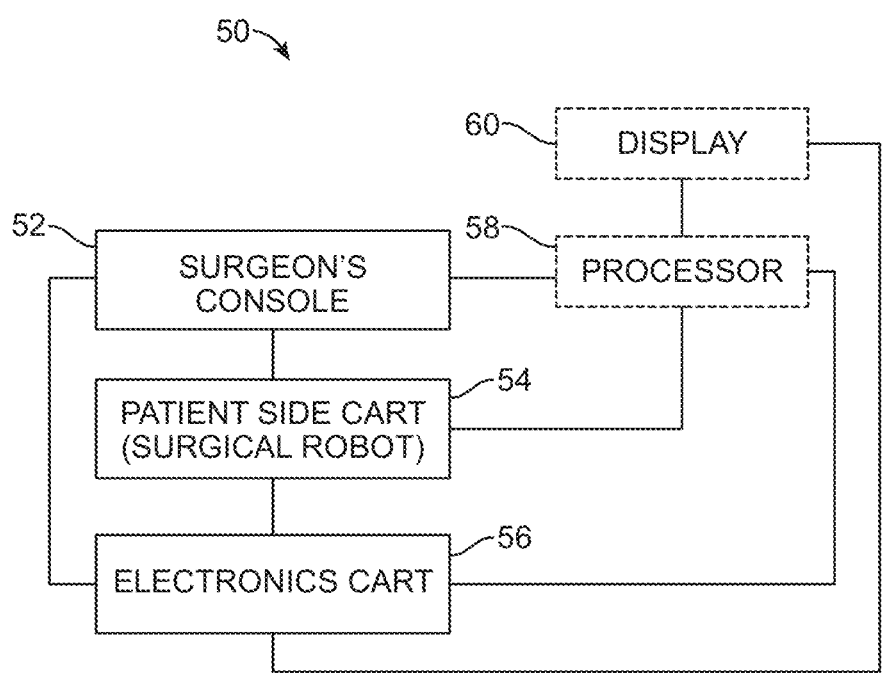
FIG. 4 is a diagrammatic illustration of a teleoperated surgical system.

FIG. 4 diagrammatically illustrates a teleoperated surgical system 50 (such as the minimally invasive teleoperated surgical system 10 of FIG. 1). As discussed above, a surgeon's console 52 (such as surgeon's console 16 in FIG. 1) can be used by a surgeon to control a patient-side cart 54 (such as patent-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The processor typically includes one or more data processing boards purposed for executing computer readable code stored in a non-volatile memory device of the processor. In one aspect, the processor can process the captured images in a variety of ways prior to any subsequent display. For example, the processor can overlay the captured images with a virtual control interface prior to displaying the combined images to the surgeon via the surgeon's console 52.

Additionally or in the alternative, the captured images can undergo image processing by a processor located outside of electronics cart 56. In one aspect, teleoperated surgical system 50 includes an optional processor 58 (as indicated by dashed line) similar to the processor located on electronics cart 56, and patient-side cart 54 outputs the captured images to processor 58 for image processing prior to display on the surgeon's console 52. In another aspect, captured images first undergo image processing by the processor on electronics cart 56 and then undergo additionally image processing by processor 58 prior to display on the surgeon's console 52. In one aspect, teleoperated surgical system 50 includes an optional display 60, as indicated by dashed line. Display 60 is coupled with the processor located on the electronics cart 56 and with processor 58, and captured images processed by these processors can be displayed on display 60 in addition to being displayed on a display of the surgeon's console 52.

Figure 5:
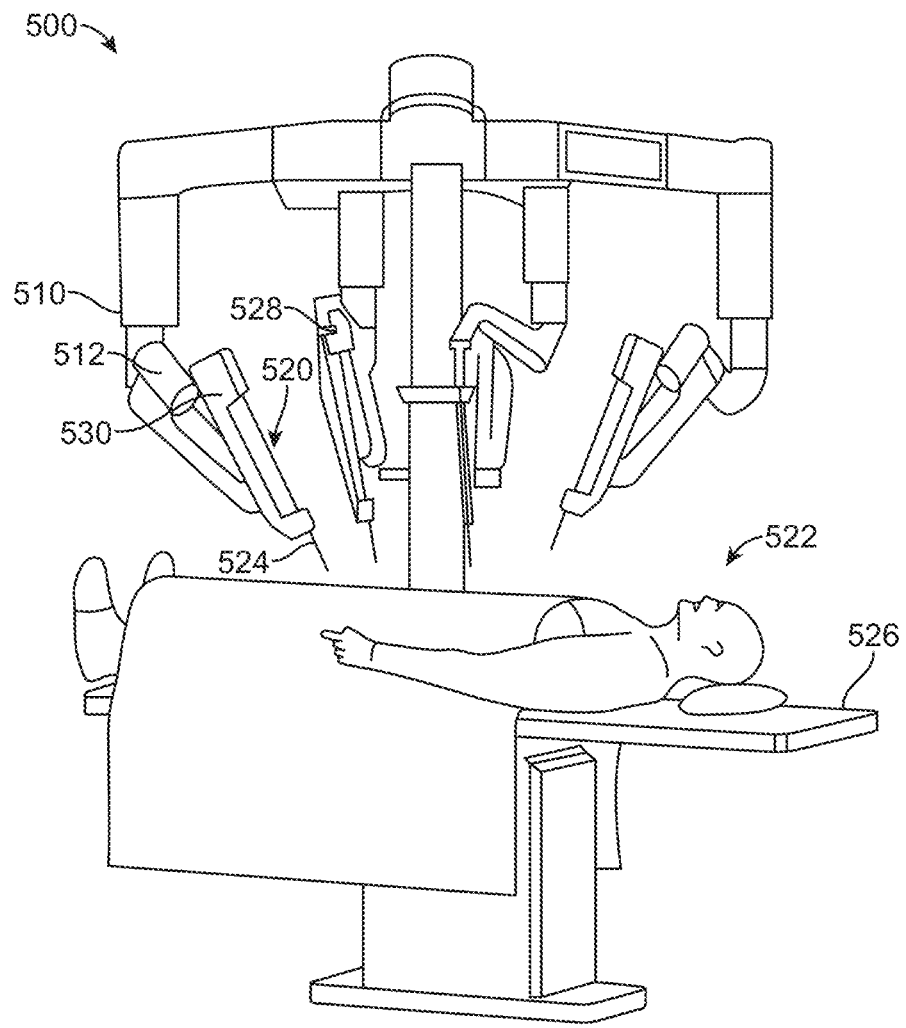
FIG. 5 is a perspective view of a patient-side cart.

FIG. 5 is a perspective view of a patient-side cart 500 of a minimally invasive teleoperated surgical system, in accordance with embodiments of the present invention. The patient-side cart 500 includes one or more support assemblies 510. A surgical instrument manipulator 512 is mounted at the end of each support assembly 510. Additionally, each support assembly 510 can optionally include one or more unpowered, lockable setup joints that are used to position the attached surgical instrument manipulator 512 with reference to the patient for surgery. As depicted, the patient-side cart 500 rests on the floor. In other embodiments, operative portions of the patient-side cart can be mounted to a wall, to the ceiling, to the operating table 526 that also supports the patient's body 522, or to other operating room equipment. Further, while the patient-side cart 500 is shown as including four surgical instrument manipulators 512, more or fewer surgical instrument manipulators 512 may be used.

A functional minimally invasive teleoperated surgical system will generally include a vision system portion that enables the operator to view the surgical site from outside the patient's body 522. The vision system typically includes a camera instrument 528 for capturing video images and one or more video displays for displaying the captured images. In some surgical system configurations, the camera instrument 528 includes optics that transfer the images from the distal end of the camera instrument 528 to one or more imaging sensors (e.g., CCD or CMOS sensors) outside of the patient's body 522. Alternatively, the imaging sensor(s) can be positioned at the distal end of the camera instrument 528, and the signals produced by the sensor(s) can be transmitted along a lead or wirelessly for processing and display on the one or more video displays. An illustrative video display is the stereoscopic display on the surgeon's console in surgical systems commercialized by Intuitive Surgical, Inc., Sunnyvale, Calif.

Referring to FIG. 5, mounted to each surgical instrument manipulator 512 is a surgical instrument 520 that operates at a surgical site within the patient's body 522. Each surgical instrument manipulator 512 can be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 512 to move its associated surgical instrument around a center of motion on the instrument that stays stationary with reference to the patient, and this center of motion is typically located at the position where the instrument enters the body.

In one aspect, surgical instruments 520 are controlled through computer-assisted teleoperation. A functional minimally invasive teleoperated surgical system includes a control input that receives inputs from a user of the teleoperated surgical system (e.g., a surgeon or other medical person). The control input is in communication with one or more computer-controlled teleoperated actuators, to which surgical instrument 520 is coupled. In this manner, the surgical instrument 520 moves in response to a medical person's movements of the control input. In one aspect, one or more control inputs are included in a surgeon's console such as surgeon's console 16 shown at FIG. 2. A surgeon manipulates input control devices 36 of surgeon's console 16 to operate teleoperated actuators of patient-side cart 500. The forces generated by the teleoperated actuators are transferred via drivetrain mechanisms, which transmit the forces from the teleoperated actuators to the surgical instrument 520.

Referring to FIG. 5, in one aspect, a surgical instrument 520 and a cannula are removably coupled to the distal end of manipulator 512, with the surgical instrument 520 inserted through the cannula 524. One or more teleoperated actuators of the manipulator 512 move the surgical instrument 512 as a whole. The manipulator 512 further includes an instrument carriage 530. The surgical instrument 520 is detachably connected to the instrument carriage 530. In one aspect, the instrument carriage 530 houses one or more teleoperated actuators that provide a number of controller motions that the surgical instrument 520 translates into a variety of movements of an end effector on the surgical instrument 520. Thus the teleoperated actuators in the instrument carriage 530 move only one or more components of the surgical instrument 520 rather than the instrument as a whole. Inputs to control either the instrument as a whole or the instrument's components are such that the input provided by a surgeon or other medical person to the control input (a "master" command) is translated into a corresponding action by the surgical instrument (a "slave" response).

In an alternate embodiment, instrument carriage 530 does not house teleoperated actuators. Teleoperated actuators that enable the variety of movements of the end effector of the surgical instrument 520 are housed in a location remote from the instrument carriage 530, e.g., elsewhere on patient-side cart 500. A cable-based force transmission mechanism or the like is used to transfer the motions of each of the remotely located teleoperated actuators to a corresponding instrument-interfacing output located on instrument carriage 530.

Figure 6:
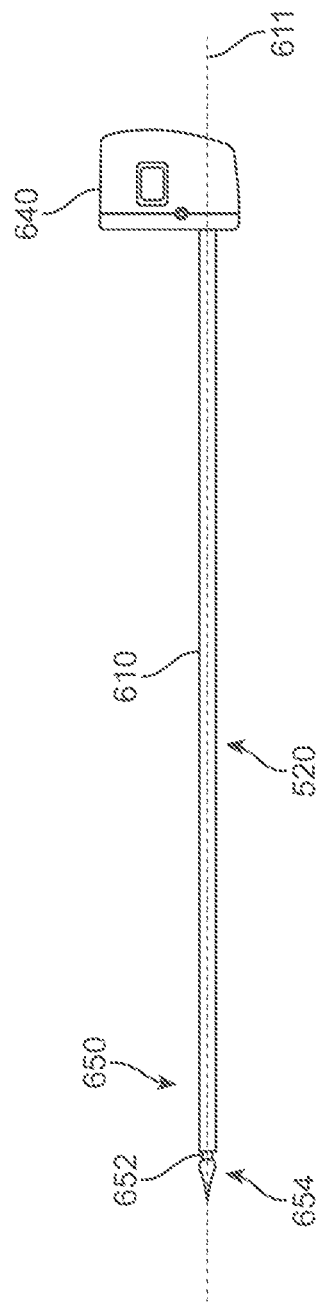
FIG. 6 is an elevation view of a surgical instrument.

FIG. 6 is a side view of a surgical instrument 520, comprising a distal portion 650 and a proximal control mechanism 640 coupled by an elongate tube 610 having an elongate tube centerline axis 611. The surgical instrument 520 is configured to be inserted into a patient's body and used to carry out surgical or diagnostic procedures. The distal portion 650 of the surgical instrument 520 can provide any of a variety of end effectors 654, such as the forceps shown, a needle driver, a cautery device, a cutting tool, an imaging device (e.g., an endoscope or ultrasound probe). In the embodiment shown, the end effector 654 is coupled to the elongate tube 610 by a wrist 652 that allows the orientation of the end effector to be manipulated with reference to the elongate tube centerline axis 611. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

Figure 7:
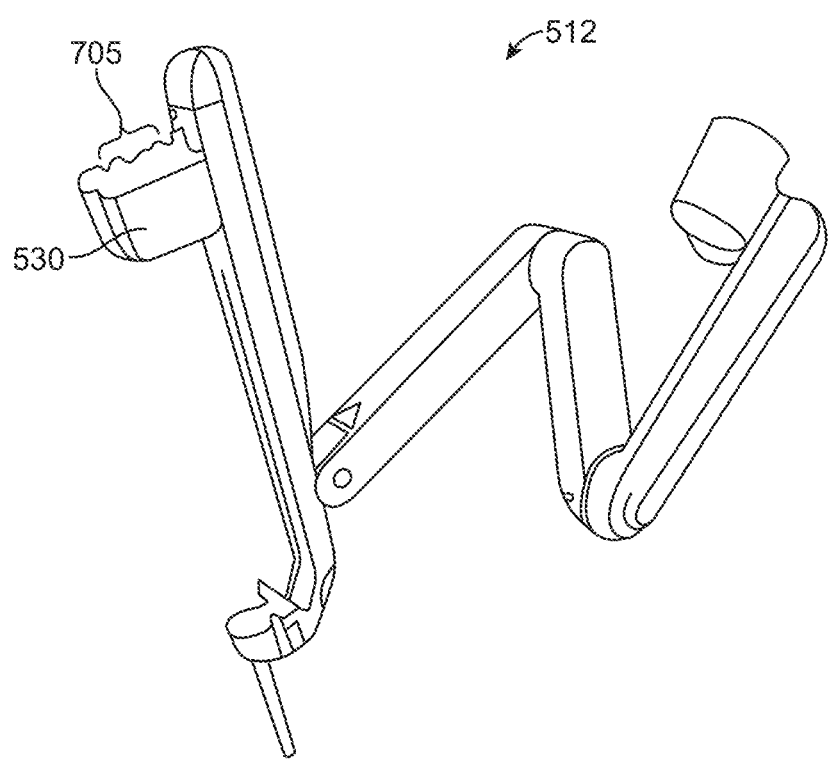
FIG. 7 is a perspective view of an instrument manipulator.

FIG. 7 is a perspective view of surgical instrument manipulator 512, which is also shown in FIG. 5 Instrument manipulator 512 is shown with no surgical instrument installed. Instrument manipulator 512 includes an instrument carriage 530 to which a surgical instrument can be detachably connected. Instrument carriage 530 houses a plurality of teleoperated actuators (not shown). Each teleoperated actuator includes an actuator output 705. When a surgical instrument is installed onto instrument manipulator 512, one or more instrument inputs (not shown) of an instrument proximal control mechanism (e.g., proximal control mechanism 640 at FIG. 6) are mechanically coupled with corresponding actuator outputs 705. In one aspect, this mechanical coupling is direct, with actuator outputs directly contacting corresponding instrument inputs. In another aspect, this mechanical coupling occurs through an intermediate interface, such as a component of a drape configured to provide a sterile barrier between the instrument manipulator 512 an associated surgical instrument.

In one aspect, movement of one or more instrument inputs by corresponding teleoperated actuators results in a movement of a surgical instrument mechanical degree of freedom. For example, in one aspect, the surgical instrument installed on instrument manipulator 512 is surgical instrument 520, shown at FIG. 6. Referring to FIG. 6, in one aspect, movement of one or more instrument inputs of proximal control mechanism 640 by corresponding teleoperated actuators rotates elongate tube 610 (and the attached wrist 652 and end effector 654) relative to the proximal control mechanism 640 about elongate tube centerline axis 611. In another aspect, movement of one or more instrument inputs by corresponding teleoperated actuators results in a movement of wrist 652, orienting the end effector 654 relative to the elongate tube centerline axis 611. In another aspect, movement of one or more instrument inputs by corresponding teleoperated actuators results in a movement of one or more moveable elements of the end effector 654 (e.g., a jaw member, a knife member, etc.). Accordingly, various mechanical degrees of freedom of a surgical instrument installed onto an instrument manipulator 512 can be moved by operation of the teleoperated actuators of instrument carriage 530.

Patient Side Control of Teleoperated Instrument End Effector

As discussed previously, FIG. 1 is a plan view of an exemplary minimally invasive teleoperated surgical system. Referring to FIG. 1, in one aspect, a surgeon 18 performs a medical procedure using a teleoperated surgical system by manipulating one or more input control devices (e.g., input control devices 36 shown at FIG. 2) of a surgeon's console 16. In this manner, surgeon 18 teleoperatively controls surgical instruments installed on patient-side cart 22, which is located some distance away from surgeon 18 seated at surgeon's console 16. In certain situations, however, it may be desirable for a medical person other than surgeon 18 (e.g., assistants 20 at FIG. 1) to have the ability to control one or more mechanical degrees of freedom of surgical instruments installed on patient-side cart 22 from a location other than surgeon's console 16. For example, it may be desirable for this control of a surgical instrument installed on patient-side cart 22 to be from beside patient 12 and patient-side cart 22 (i.e., to have patient-side control of the surgical instrument). It may also be desirable for this control of the surgical instruments by persons other than surgeon 18 to have minimal disruption on surgical workflow.

Figure 8A:
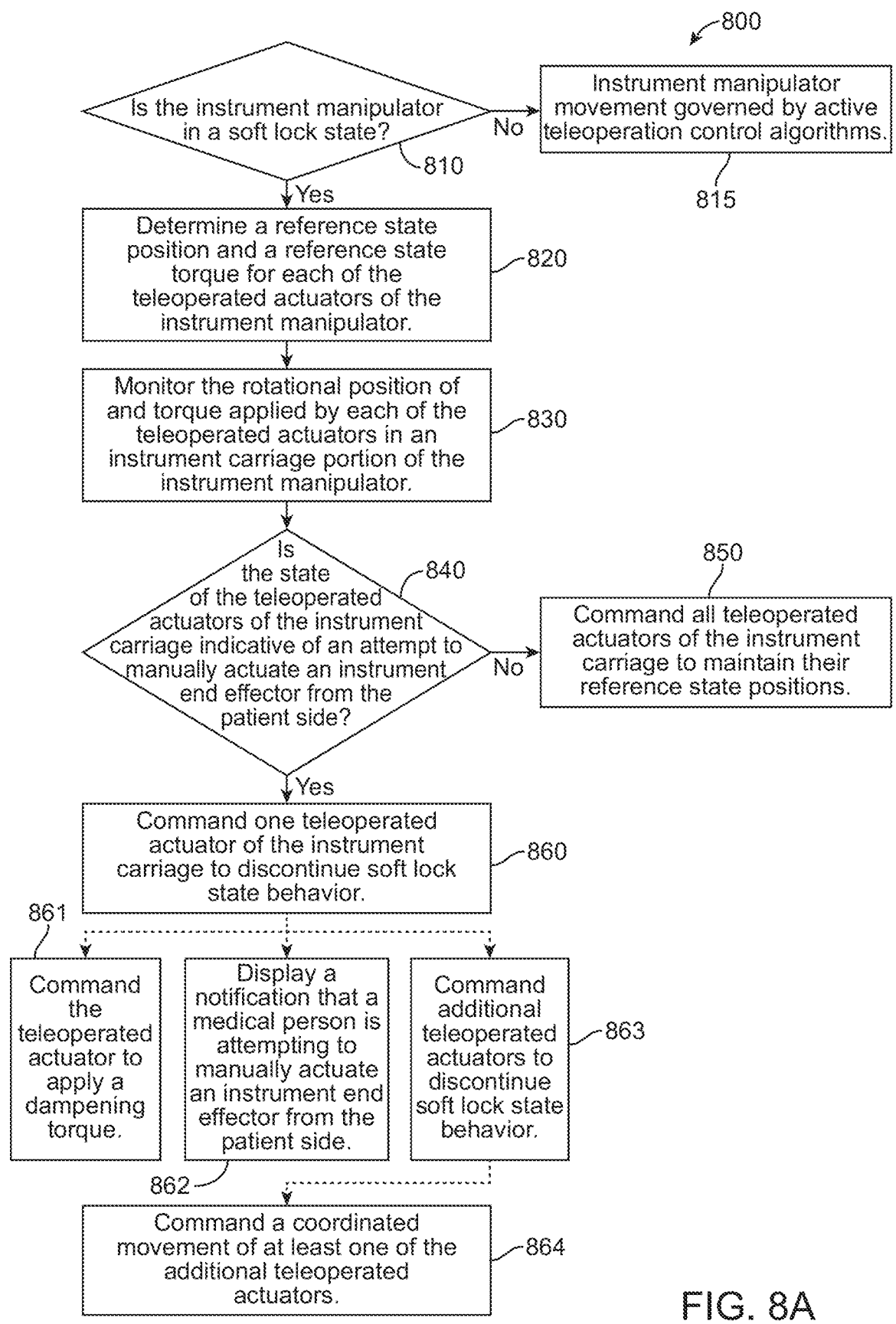
FIG. 8A is a schematic diagram of a control algorithm that enables patient side control of a teleoperated surgical instrument.

FIG. 8A is a flow diagram of a control algorithm 800 implemented on a minimally invasive teleoperated surgical system. In one aspect, the teleoperated surgical system is similar to teleoperated surgical system 10 at FIG. 1. Control algorithm 800 enables a medical person to control, from a location beside the patient rather than from a surgeon's console (e.g., surgeon's console 16 shown at FIG. 1), a mechanical degree of freedom of a surgical instrument (e.g., instrument 520 shown at FIG. 6) installed on a patient-side cart (e.g., patient-side cart 500 shown at FIG. 5). In one aspect, algorithm 800 is enabled only for patient-side cart instrument manipulators that are in a soft lock state. An instrument manipulator is in a soft lock state when the instrument manipulator is commanded by software to remain stationary in space. To say that a manipulator is in a soft lock state is another way of saying that it in a software lock state. This definition of soft lock state (or software lock state) can be understood in contrast to a hardware lock, in which a physical brake is used to maintain the position of one or more movable elements. Generally, in the absence of external forces, an instrument installed on an instrument manipulator in soft lock state does not experience any movement.

Referring to FIG. 1, in one aspect, computer-assisted active teleoperation occurs when a surgeon 18 remotely controls the movement of surgical instruments mounted on patient-side cart 22. In one aspect, during active teleoperation, surgeon 18 manipulates one or more input control devices (e.g., input control devices 36 at FIG. 2) of a surgeon's console 16. One or more computer processors interpret the movement of the one or more input control devices, and communicate this information to one or more instrument manipulators coupled to the one or more input control devices. Teleoperated actuators located on the one or more instrument manipulators move in response to the movements of the input control devices. As discussed previously, a surgical instrument can be installed onto the instrument carriage of an instrument manipulator. By mechanically coupling one or more instrument inputs to corresponding actuator outputs (e.g., actuator outputs 705 at FIG. 7) of teleoperated actuators, various mechanical degrees of freedom of a surgical instrument installed onto an instrument manipulator can be controlled by a surgeon 18 seated at the surgeon's console 16.

In one aspect, a computer processor of a minimally invasive teleoperated surgical system (e.g., a computer processor located on electronics cart 24 shown at FIG. 3) queries a patient-side cart with one or more instrument manipulators to determine whether algorithm 800 is enabled for each of the one or more instrument manipulators. Referring to FIG. 8A, in one aspect, algorithm 800 at 810 determines if an instrument manipulator is in a soft lock state by determining whether a particular instrument manipulator is receiving movement commands associated with a surgeon's manipulating one or more control inputs at a surgeon's console. If the instrument manipulator is not in a soft lock state, then at 815, instrument manipulator movement is governed by active teleoperation control algorithms.

In one aspect, algorithm 800 determines a reference state for an instrument manipulator. A surgical instrument is installed on the instrument manipulator, and the manipulator is in a soft lock state. Referring to FIG. 8A, algorithm 800 at 820 determines a reference state for a plurality of teleoperated actuators housed in the carriage portion (e.g., instrument carriage 530 at FIG. 5 and FIG. 7) of the instrument manipulator (e.g., instrument manipulator 520 at FIG. 5 and FIG. 7). In one aspect, the teleoperated actuators are teleoperated servo motors, and the reference state includes the rotational position of each servo motor drive shaft (the drive shaft reference state position) and the torque being applied by each servo motor to maintain its rotational position (the reference state torque). Generally, in the absence of external forces, the instrument installed on the instrument manipulator in soft lock state does not experience any movement. The instrument manipulator holds the instrument's mechanical degrees of freedom static, applying to each servo motor its reference state torque to maintain each servo motor's drive shaft reference state position.

At 830, the rotational position and torque applied by each of the plurality of teleoperated servo motors is continuously monitored. One or more instrument inputs of the surgical instrument are mechanically coupled to corresponding teleoperated servo motors. In one situation, external forces are applied to an end effector (e.g., end effector 654 at FIG. 6) located at a distal end of the instrument, e.g., due to a second instrument's collision with the end effector, and the external forces applied to the end effector back-drive one or more instrument inputs in the following manner. The external forces are transferred from the end effector through a drive mechanism (e.g., pullwires, tendons, pulleys, gears, etc.) of the instrument to one or more instrument inputs that control movement of the end effector, and the forces are further transferred by the instrument inputs to corresponding teleoperated servo motors with which the instrument inputs are mechanically coupled.

Algorithm 800 at 840 determines that the forces transmitted to the servo motors are indicative of external forces applied to the end effector, and that the forces transmitted to the servo motors are not indicative of a deliberate attempt by a medical person to manually actuate the instrument end effector from the patient side. In one aspect, this determination at 840 is made if two or more servo motors (as opposed to only a single servo motor) experience force perturbations that cause the two or more servo motors to be incapable of maintaining their respective drive shaft reference state positions without applying torques in excess of their respective reference state torques. In such case, algorithm 800 proceeds to 850, at which all servo motors of the instrument carriage onto which the instrument is installed are commanded to remain in the soft lock state. Each servo motor is generally commanded to maintain its drive shaft reference state position, applying additional torque as necessary to counteract the external force. In this manner, the position and orientation of the instrument end effector is maintained despite the external force applied to the instrument end effector.

In one aspect, a torque limit exists for at least one of the servo motors. If an external force causes a servo motor with a torque limit to be acted upon by a torque in excess of this torque limit, the servo motor will be incapable of resisting the torque generated by the external force. One way of implementing a torque limit for a servo motor is through software control. Each servo motor can include a rotary encoder that is capable of detecting the rotational position of the drive shaft of the servo motor. The torque applied by the servo motor is a function of the electrical current supplied to the servo motor. Accordingly, the servo motors can be controlled using the drive shaft rotational position and the electrical current supplied to the servo motor. For example, 1 ft-lb torque limit implemented using software control can be set for a servo motor. Accordingly, the servo motor can be commanded to maintain its rotational position subject to an upper limit to the electrical current applied to the servo motor. This upper limit to the electrical current corresponds to the 1 ft-lb torque limit. If the servo motor is exposed to external forces that causes it to be subject to greater than 1 ft-lb of torque, the torque limit precludes the servo motor from maintaining is rotational position. As a result, the servo motor will be back driven away from the rotational position it was trying to maintain. If the torque that the servo motor is subject to drops below 1 ft-lb, then the servo motor is again able to return to the rotational position it was trying to maintain.

In one aspect, a surgical instrument (e.g., surgical instrument 520 at FIG. 6) provided for use with a minimally invasive teleoperated surgical system includes mechanical features for manual actuation of an end effector of the surgical instrument. The mechanical features can include a lever (e.g., lever 910 at FIG. 9A) operable by a medical person to actuate an instrument end effector. Alternatively, the mechanical features can include a socket head feature (e.g., socket head feature 1020a at FIG. 10B) with which a hex wrench can be engaged to rotate a rotatable member. The lever or socket head feature can be mechanically coupled to an instrument input by a mechanism including at least one of a pullwire, tendon, pulley, gears, etc. When the surgical instrument is installed for use on a teleoperated surgical system, the instrument input is mechanically coupled to a servo motor. Additional aspects of various mechanical features for manual end effector actuation will be discussed in greater detail later with reference to FIGS. 9-12.

In one aspect, a teleoperated surgical system is configured to allow a medical person to use manually actuate an end effector of a surgical instrument while the instrument is installed on a patient-side cart instrument manipulator, provided that the instrument manipulator is in the soft lock state. A medical person can apply an external force to a mechanical feature of a surgical instrument (e.g., lever 910 at FIG. 9A, socket head feature 1020a at FIG. 10B, etc.) configured to provide manual actuation of an end effector of the surgical instrument, while the surgical instrument is installed on a patient-side cart instrument manipulator. As discussed previously, when a surgical instrument is installed for use on a teleoperated surgical system, one or more instrument inputs are mechanically engaged with corresponding actuator outputs of servo motors. Accordingly, the external force applied by the medical person is mechanically transmitted (e.g., by pullwires, tendons, pulleys, gears, etc.) to an instrument input, which in turn transmits a force to a teleoperated servo motor with which the instrument input is mechanically coupled.

In one aspect, algorithm 800 at 840 detects that one servo motor (as opposed to two or more servo motors) experiences force perturbations that cause the one servo motor to be incapable of maintaining its drive shaft reference state position without applying torque in excess of its respective reference state torque, and determines that this is indicative of a deliberate attempt by a medical person to manually actuate the instrument from the patient side (i.e., it is not indicative of an external force applied to an end effector of the instrument). In such case, algorithm 800 proceeds to 860, at which the one servo motor is commanded to discontinue soft lock state behavior. The behavior of the other servo motors are not affected. They remain in the soft lock state, in which they are commanded to apply additional torque as necessary to maintain their respective drive shaft reference state positions. For the one servo motor, that one servo motor will not be commanded to apply larger torque in order to maintain its drive shaft reference state position. In one aspect, power to this one servo motor will be cut off. Accordingly, the external force applied by the medical person to manually actuate the end effector overcomes any passive resistance of the powered-off servo motor and successfully actuates the end effector.

In another aspect, after a servo motor is commanded to discontinue soft lock behavior at 860, algorithm 800 at 861 may optionally (as indicated by dashed line) command the servo motor to apply a torque to resist or dampen the effects of external forces applied by a medical person to manually actuate the end effector. This torque applied by the servo motor is in a direction opposite to and has a magnitude that is less than the torque acting on the servo motor as a result of the external forces applied by the medical person. Application of this resistive/dampening torque enables an enhanced degree of control over the speed at which manual actuation of the instrument end effector takes place. For instance, while cutting power to the servo motor is alone sufficient to allow a medical person to back-drive the servo motor and manually actuate the end effector, the teleoperated surgical system on which algorithm 800 is implemented retains no control over the speed at which the manual actuation of the end effector takes place. In contrast, if algorithm 800 includes 861, the servo motor can, e.g., apply a torque having an appropriate magnitude to slow down a manual actuation by a medical person when the algorithm detects an attempted manual actuation of the end effector that is quicker than preferred for safety purposes. This aspect is further discussed later with reference to FIGS. 9A-9B.

In one aspect, after a servo motor is commanded to discontinue soft lock behavior at 860, algorithm 800 at 862 may optionally (as indicated by dashed line) instruct the teleoperated surgical system to provide a notification that a medical person is attempting to manually actuate the end effector of an instrument installed for use on the teleoperated surgical system. Referring to FIGS. 1-3, this notification can be a visual notification provided to surgeon 18 via at least one of left eye display 32 and right eye display 34 of surgeon's console 16. This notification can also be a visual notification provided via a visual display of electronics cart 24. This notification can also be an auditory notification, e.g., in the form of a warning message that can be heard by an operating surgeon or by all members of a surgical team.

In one aspect, a surgical instrument installed for use on a teleoperated surgical system implementing algorithm 800 includes an end effector having multiple mechanical degrees of freedom that are operated by two or more instrument inputs. FIGS. 11A-11C and 12A-12C show various aspects of this type of surgical instrument. When the surgical instrument is installed for use on a teleoperated surgical system, the two or more instrument inputs that operate the multiple mechanical degrees of freedom are mechanically engaged with corresponding servo motors.

In one aspect, a medical person desires to manually actuate the multiple mechanical degrees of freedom of the instrument end effector from the patient side, while the instrument is installed on the teleoperated surgical system. In one aspect, the medical person manually actuates the multiple mechanical degrees of freedom by applying a first external force to a first mechanical feature mechanically coupled to a first instrument input by a mechanism including at least one of a pullwire, tendon, pulley, gears, etc., and then applying a second external force to a second mechanical feature similarly coupled to a second instrument input. One or more additional mechanical features similarly coupled to additional instrument inputs may be included. Accordingly, in one aspect, after a first servo motor is commanded to discontinue soft lock behavior at 860, algorithm 800 at 863 may optionally (as indicated by dashed line) command one or more additional servo motors to discontinue soft lock behavior. In one aspect, power to the first servo motor and the one or more additional servo motors will be cut off. In this manner, the external forces applied by the medical person (e.g., the first external force and the second external force) to manually actuate the end effector overcomes any passive resistance of powered-off servo motor and successfully actuates the multiple degrees of freedom in series. Various aspects are discussed later in greater detail with reference to FIGS. 12A-12C.

Figure 11A:
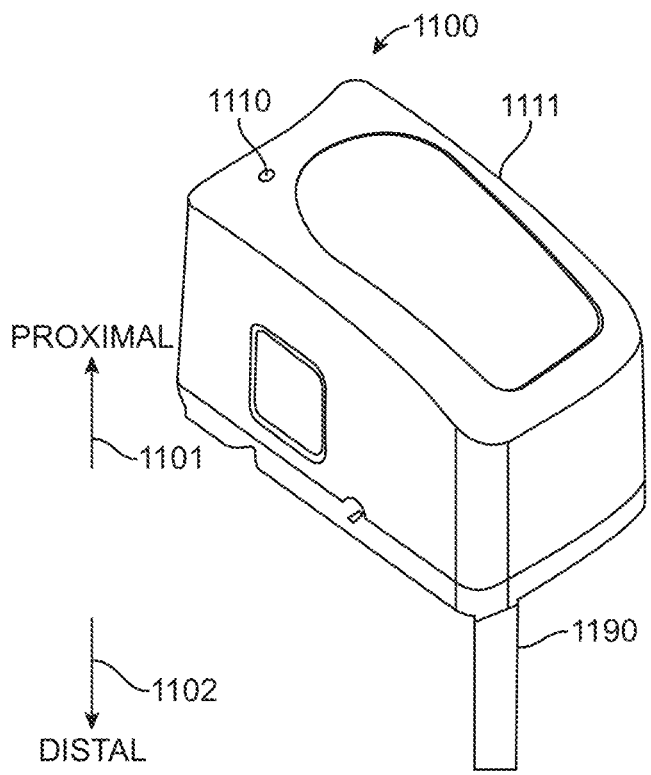
FIG. 11A is a perspective view of a proximal control portion of a surgical instrument.
Figure 11B:
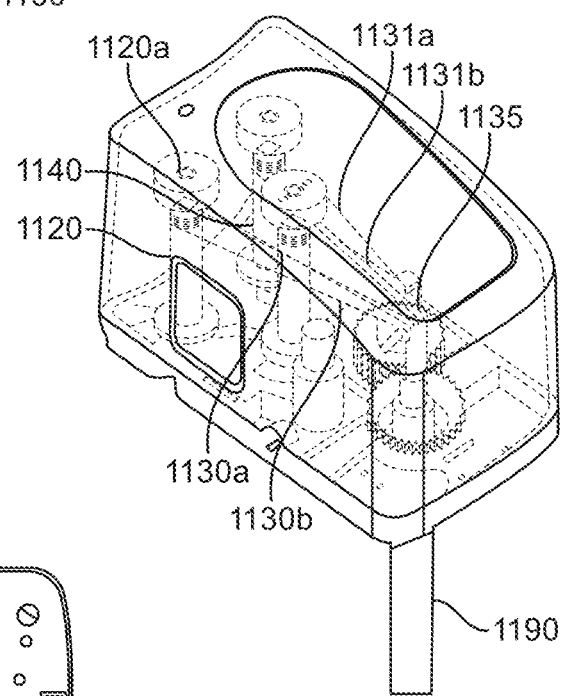
FIG. 11B is a perspective view of a proximal portion of a surgical instrument with its exterior cover shown transparently.
Figure 11C:
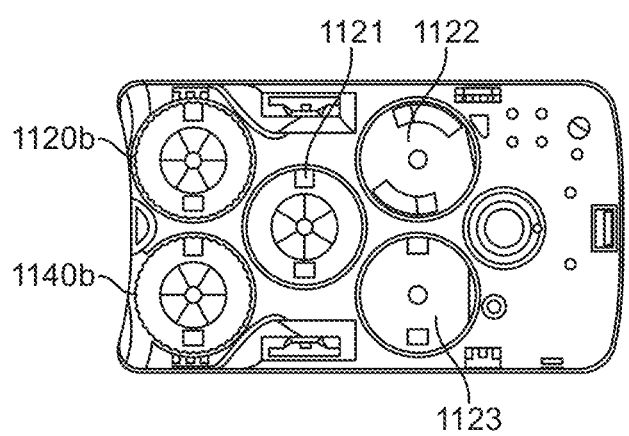
FIG. 11C is a proximal control portion of a surgical instrument viewed from the distal direction.

In one aspect, a surgical instrument installed for use on a teleoperated surgical system implementing algorithm 800 includes an end effector having two independently controllable mechanical degrees of freedom. On example of such a surgical instrument is a two jaw instrument, in which the movement of each of the two jaws is controlled by a separate instrument input of an instrument proximal control mechanism (e.g., proximal control mechanism 640 at FIG. 6). One embodiment of a two jaw instrument proximal control mechanism is shown at FIGS. 11A-11C.

In one aspect, a two jaw instrument of the type described above is installed for use on a teleoperated surgical system. A medical person applies an external force to a mechanical feature of the two jaw instrument configured to provide manual actuation one of the two jaws. This external force applied by the medical person is mechanically transmitted (e.g., by pullwires, tendons, pulleys, gears, etc.) to a first instrument input, which in turn transmits a force to a corresponding first teleoperated servo motor. Consistent with earlier discussions with reference to 840 and 860, in one aspect, the first teleoperated servo motor is commanded to discontinue soft lock behavior at 860.

In one aspect, when a medical person desires to manually actuate an end effector of a two jaw instrument from the patient side, it is desirable for both jaws of the two jaw instrument to be actuated in a symmetrical manner. After a first servo motor is commanded to discontinue soft lock behavior at 860, algorithm 800 at 863 may optionally (as indicated by dashed line) command a second servo motor to discontinue soft lock behavior. The first servo motor is associated with a first instrument input that operates a first jaw member, and the second servo motor is associated with a second instrument input that operates a second jaw member. An external force applied by the medical person is mechanically transmitted (e.g., by pullwires, tendons, pulleys, gears, etc.) to a first instrument input, which in turn transmits the force to a corresponding first servo motor. This external force moves the first jaw member, overcoming any resistance provided by the first servo motor.

In one aspect, a controller monitors the change in rotational position of the first servo motor as it is acted upon by the medical person's manual actuation. Additionally, as indicated by dashed line, algorithm 800 at 864 may optionally actively command the second servo motor to mirror the first servo motor's change in rotational position. Accordingly, as a medical person manually actuates a movement of a first jaw member of a two jaw instrument installed for use on a teleoperated surgical system, the teleoperated surgical system commands a movement of a second jaw member of the two-jaw instrument. In one aspect, these movements produce a symmetric opening of the first jaw member and the second jaw member. Aspects of 864 are discussed in greater detail later with reference to FIGS. 11A-11C.

In one aspect, after a servo motor is commanded to discontinue soft lock behavior at 860 and after a medical person manually actuates an end effector mechanical degree of freedom associated with the servo motor, the teleoperated surgical system implementing algorithm 800 allows the instrument to immediately return to teleoperative control. Referring to FIG. 1, in one aspect, assistant 20 manually actuates the end effector of an instrument 26 in a manner consistent with the foregoing discussion. Upon assistant 20 completing the manual actuation of the end effector, surgeon 18 seated at surgeon's console 16 is immediately able to teleoperatively control instrument 26, with no disruption to the surgical workflow.

Figure 8B:
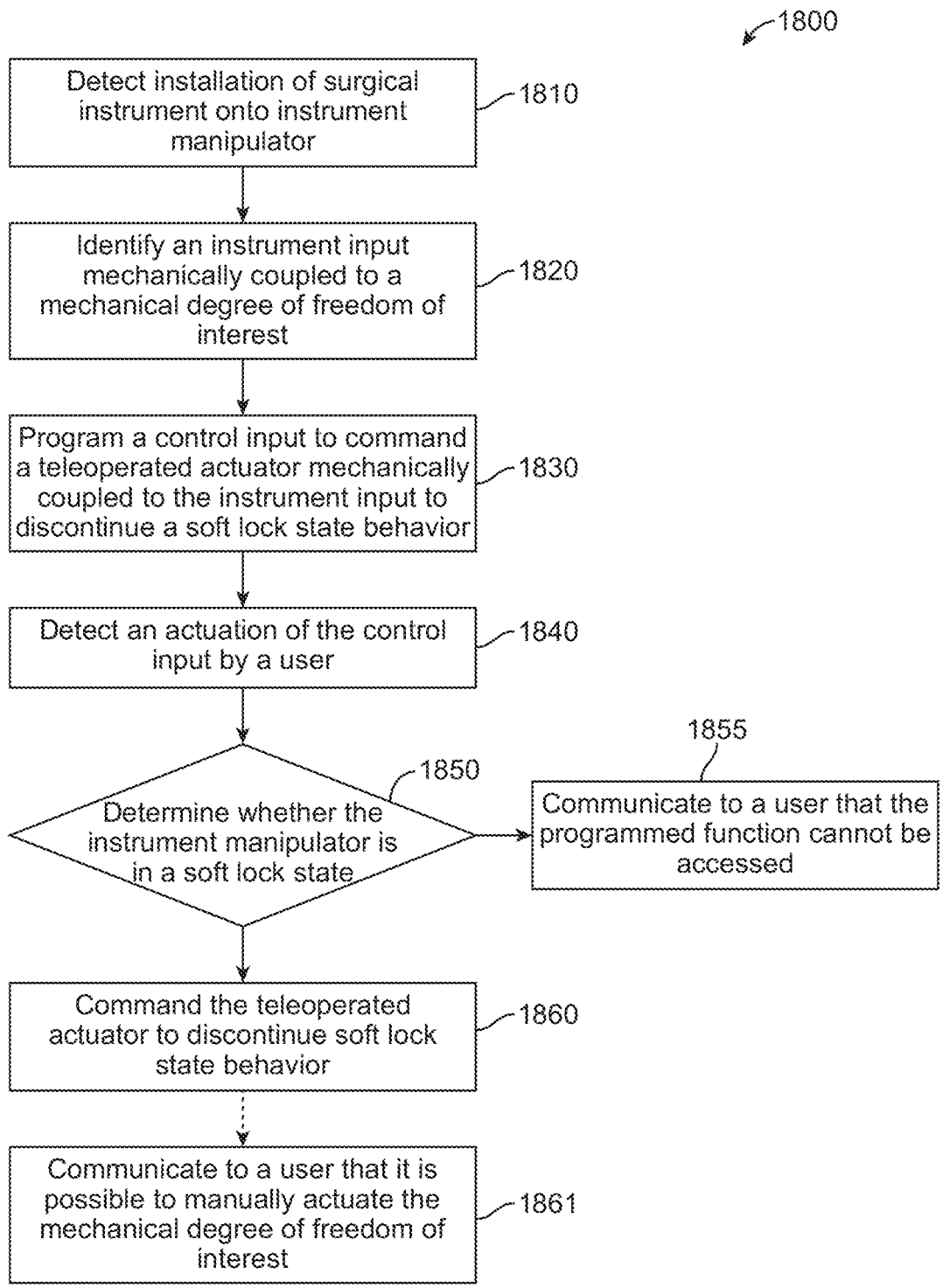
FIG. 8B is a schematic diagram of a control algorithm that enables patient side control of a teleoperated surgical instrument.

FIG. 8B is a flow diagram of a control algorithm 1800 implemented on a minimally invasive teleoperated surgical system. In one aspect, the teleoperated surgical system is similar to teleoperated surgical system 10 at FIG. 1. Like control algorithm 800 shown at FIG. 8A, control algorithm 1800 enables a medical person to control, from the patient-side, a mechanical degree of freedom of a surgical instrument (e.g., instrument 520 shown at FIG. 6) installed on a patient-side cart (e.g., patient-side cart 500 shown at FIG. 5).

Referring to FIG. 8B, at 1810, algorithm 1800 detects that a surgical instrument has been installed onto a carriage of a manipulator located on the patient-side cart of a teleoperated surgical system. Installation of the surgical instrument onto the carriage activates a sensor located on the manipulator. In one example, the sensor is a switch, and installation of the surgical instrument moves the switch from an OFF position to an ON position. Movement of the switch into the ON position causes the sensor to communicate a signal to the computer processor implementing algorithm 1800, informing it that a surgical instrument has been installed. In another instance, the sensor is a Hall effect sensor housed in the carriage, and the surgical instrument includes a magnet configured to interact with the Hall effect sensor. When the surgical instrument is installed on the manipulator, the magnet on the surgical instrument is brought into proximity with the Hall effect sensor. The proximity of the magnet causes the Hall effect sensor to communicate a signal to the computer processor implementing algorithm 1800, informing it that a surgical instrument has been installed.

In one aspect, installing the surgical instrument onto the manipulator mechanically couples one or more instrument inputs to corresponding actuator outputs (e.g., actuator outputs 705 at FIG. 7) of teleoperated actuators. The teleoperated actuators can be servo motors. During computer-assisted teleoperation, servo motors of the manipulator move in response to the movements of input control devices accessible to a user of the teleoperated surgical system. In this manner, various mechanical degrees of freedom of the surgical instrument can be controlled by a surgeon seated at a surgeon's console. See portions of this Detailed Description relating to FIGS. 1-7 for details. The surgical instrument can also include a memory device. Installing the surgical instrument onto the manipulator puts the memory device in data communication with a computer processor of the teleoperated surgical system. The memory device includes preprogrammed information, which once communicated to the teleoperated surgical system, is used to enable the computer-assisted teleoperation of the surgical instrument. The preprogrammed information is stored on the memory device of the surgical instrument at the time of the surgical instrument's manufacture.

At 1820, algorithm 1800 queries the memory device of the installed surgical instrument, whose preprogrammed information is communicated to the computer processor implementing algorithm 1800. In one aspect, the preprogrammed information communicated to the computer processor includes the type of the surgical instrument. The preprogrammed information can also include certain information used to enable computer-assisted teleoperation of the surgical instrument, such as information about the surgical instrument movements controlled by individual instrument inputs and their corresponding servo motors of the manipulator. For example, for a first instrument type, this information can include the following: (1) the instrument includes five movable instrument inputs numbered #1 through #5; (2) instrument input #1 is mechanically coupled to the mechanical degree of freedom of interest, here a mechanical degree of freedom of an end effector of the surgical instrument; and (3) instrument input #1 is mechanically driven by a corresponding servo motor #1. As another example, for a second instrument type, this information can include the following: (1) the instrument includes four movable instrument inputs numbered #1 through #4; (2) instrument input #4 is mechanically coupled to the mechanical degree of freedom of interest, here a mechanical degree of freedom that orients the end effector relative to the rest of the instrument; and (3) instrument input #4 is mechanically driven by a corresponding servo motor #4. In one aspect, at 1820, algorithm 1800 queries the memory device of the surgical instrument to determine the type of surgical instrument installed and the associated information.

At 1830, algorithm 1800 programs a manipulator control input located on an instrument manipulator of the teleoperated surgical system using to the instrument information received from the memory device of the installed instrument. In one aspect, the manipulator control input is programmed so that activating the control input commands one servo motor of the carriage controlling a mechanical degree of freedom of interest to discontinue soft lock state behavior. In one aspect, power to this servo motor is cut off. In one instance, the surgical instrument mechanical degree of freedom of interest is a mechanical degree of freedom of a surgical instrument end effector. In another instance, the surgical instrument mechanical degree freedom of interest orients the surgical instrument end effector relative to the rest of the instrument.

At 1840, algorithm 1800 detects that a user has activated the manipulator control input of an instrument manipulator with an instrument installed onto its carriage. At 1850, algorithm 1800 queries the instrument manipulator to determine whether it is in a soft lock state. If it is determined that the instrument manipulator is not in a soft lock state, algorithm 1800 proceeds to 1855, at which a message is communicated to one or more users of the teleoperated surgical system that the programmed function of the manipulator control input cannot be accessed because the manipulator is under the active control of a surgeon from the surgeon's console. In one aspect, this communication is in the form of a message displayed on one or more displays of the teleoperated surgical system. In another aspect, this communication is auditory (e.g., a voice message, an error beep, etc.). In contrast, if it is determined that the algorithm is in a soft lock state, then algorithm 1800 will allow the programmed function of the manipulator control input to be accessed, and proceeds to 1860. In one aspect, the manipulator control input is programmed to discontinue the supply of power to servo motor #1, which operates a grip mechanism of the installed surgical instrument.

Optionally, as indicated by dashed line, at 1861, algorithm 1800 communicates to one or more users of the teleoperated surgical system that it is now possible to manually actuate a grip mechanism of the installed surgical instrument from the patient-side.

First Example

Figure 9A:
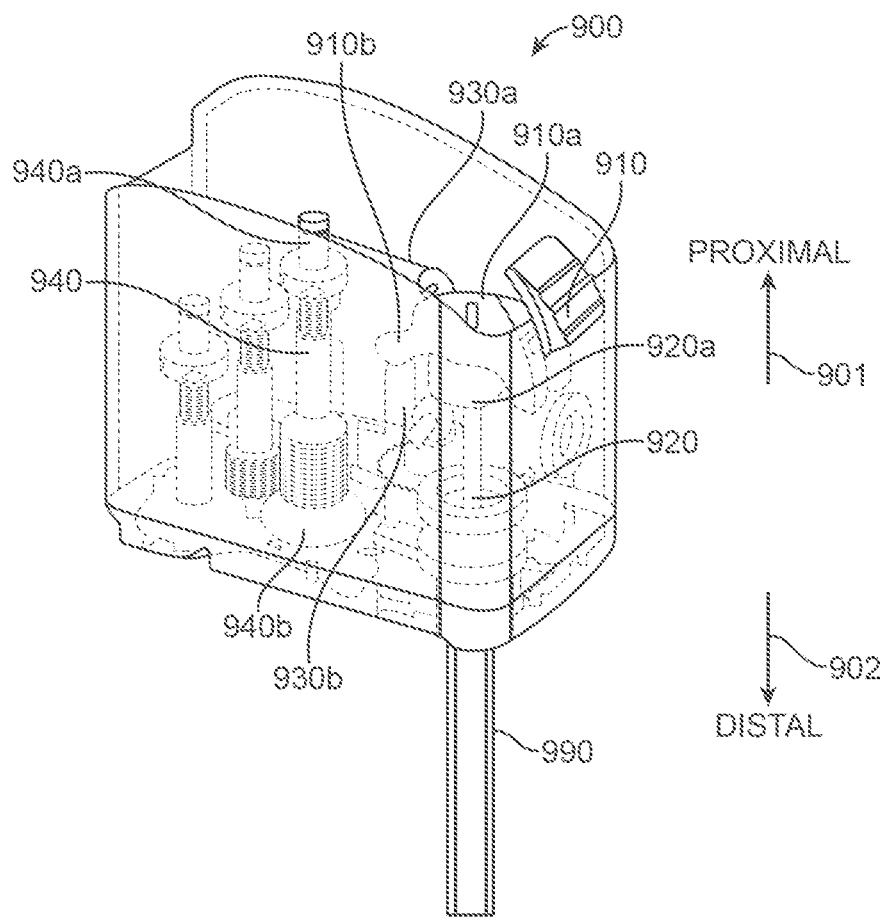
FIG. 9A is perspective view of a proximal control portion of a surgical instrument.
Figure 9B:
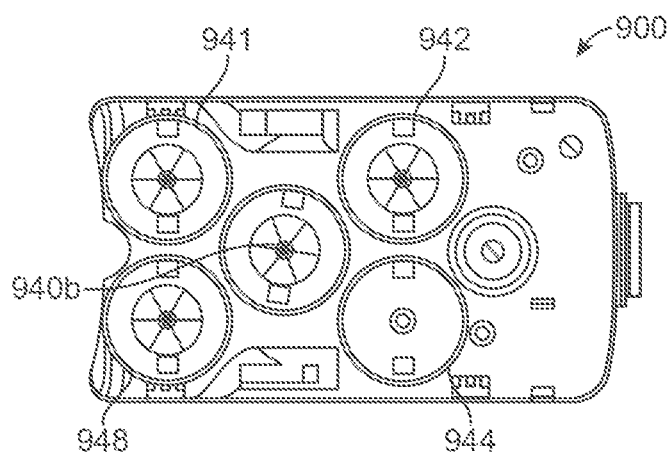
FIG. 9B is a proximal control portion of a surgical instrument viewed from the distal direction.

FIG. 9A shows a perspective view of a surgical instrument 900. FIG. 9B shows a view of instrument 900 looking from the distal 902 direction towards the proximal 901 direction. In one aspect, consistent with the foregoing discussion, instrument 900 is removably coupled to an instrument carriage (similar to instrument carriage 530 at FIG. 7) of an instrument manipulator. The instrument carriage includes a plurality of servo motors. Each of instrument inputs 940*b*, 941,942,944,948 is mechanically coupled with one of a plurality of actuator outputs (similar to actuator outputs 705 at FIG. 7) of the servo motors. Accordingly, rotation of a servo motor rotates its associated actuator output 705, which in turn rotates a corresponding instrument input (i.e., one of instrument inputs 940*b*,941,942,944,948).

Rotation of instrument input 940*b* by a corresponding servo motor opens and closes a jaw-type end effector of instrument 900. Rotation of instrument input 940*b* turns input shaft 940. Cable segment 930*a* is coupled to member 920*a*. Rotation of input shaft 940 in a first direction will increase tension in cable segment 930*a* and reduce tension in cable segment 930*b*, moving member 920 in the proximal direction and applying a force to close the end effector jaws of instrument 900. Rotation of input shaft 940 in a second direction will increase tension in cable segment 930*b* and reduce tension in cable segment 930*a*, moving member 920 in the distal direction and applying a force to open the end effector jaws of instrument 900.

In one aspect, instrument 900 is installed on an instrument carriage component of an instrument manipulator, and instrument inputs 940*b*,941,942,943,944 are mechanically coupled to corresponding servo motors of the carriage portion of the instrument manipulator. The servo motors of the instrument manipulator are in a soft lock state, and not being actively controlled by a surgeon or other medical person. A reference state is determined for the plurality of servo motors of instrument carriage. The reference state notes for each servo motor the rotational position of the servo motor drive shaft and the torque being applied by the servo motor to maintain the position of the motor.

In one aspect, a medical person located at the patient side desires to open the end effector jaws of instrument 900 while instrument 900 is installed for use on the instrument carriage. Referring to FIG. 9A, in one aspect, the medical person opens the end effector jaws of instrument 900 by actuating lever 910. Lever 910 is coupled to member 910*a*. Actuating lever 910 by moving it in the distal 902 direction causes member 910*a* to pivot about axis 910*b*. The pivoting of member 910*a* produces a movement of member 910*a* that is generally in the distal 902 direction. This distal movement is transferred to elongate member 920 by feature 920*a*. Elongate member 920 transmits this force down the shaft 990 of the instrument to actuate end effector jaws of instrument 900. Actuating lever 910 by moving it in the distal 902 direction also applies cable tension to cable segment 930*a* and releases cable tension in cable segment 930*b*. This in turn causes cable to unwind from capstan 940*a* as input shaft 940 rotates. The rotational force applied to input shaft 940 is transmitted via instrument input 940*b* (directly, or through an intermediate interface) to a corresponding servo motor in instrument carriage 705.

In one aspect, the instrument manipulator to which instrument 900 is installed is in a soft lock state. Generally, in the soft lock state, a controller of the instrument manipulator commands each servo motor of the instrument manipulator to maintain each servo motor's drive shaft rotational position. If the servo motor operatively coupled to instrument input 940*b* remains in a soft lock state when a medical person actuates lever 910, then the associated servo motor will simply be commanded to increase the amount of motor torque applied an equal and opposite amount, so as to maintain the servo motor at its drive shaft reference state position. If the servo motor operatively coupled to instrument input 940*b* stays in a soft lock state, the medical person actuating lever 910 will likely be unable to open the end effector jaws of instrument 900, unless he applies sufficient torque through instrument input 940*b* to overcome a torque limit of the associated servo motor.

In one aspect, as discussed in the context of algorithm 800 with reference to FIG. 8A, certain conditions detectable at the servo motors are indicative of a medical person attempting to operate the end effector from the patient side. In such case, a controller of the instrument manipulator will disable soft lock in one or more servo motors so as to enable an external force applied by a medical person to back-drive the one or more servo motors. Referring to FIG. 9A, in one aspect, instrument input 944 is configured to rotate instrument shaft 990 about an instrument shaft longitudinal axis. In one aspect, instrument 900 is installed on and operatively coupled to an instrument carriage of an instrument manipulator in a soft lock state. Upon entering soft lock state, a reference state is taken, including the drive shaft rotational position (drive shaft reference state position) of each of the servo motors of the instrument carriage and the torque applied by each of the servo motors (reference state torque) to maintain its respective drive shaft reference state position.

After the drive shaft reference state position and the reference state torque of each servo motor are taken, a medical person applies an external force via lever 910 that acts on the servo motor corresponding to instrument input 940*b*. The external force cause the servo motor to be incapable of maintaining its drive shaft reference state position without applying torque in excess of its reference state torque. In one aspect, the controller further detects that the drive shaft rotational position of the servo motor corresponding to instrument input 944 (instrument shaft roll) is unchanged from its drive shaft reference state position, and that the torque applied by the servo motor corresponding to instrument input 944 remains its reference state torque. In response, the servo motor mechanically coupled to instrument input 940*b* is commanded to discontinue soft lock state behavior. In one aspect, power to the servo motor is cut off. Accordingly, the external force applied by the medical person's actuation of lever 910 overcomes any passive resistance of the powered-off servo motor and successfully opens the end effector jaws of instrument 900.

In one aspect, after a particular servo motor is commanded to discontinue soft lock state behavior, power to the servo motor is not cut off. Instead, the servo motor is commanded to actively apply a torque to resist the back-driving of the instrument input coupled to the servo motor, similar to 861 at FIG. 8A. For instance, referring to FIG. 9A and FIG. 9B, in one aspect, a medical person actuates lever 910 and applies an external force to instrument input 940*b*, acting on it to rotate in a counterclockwise direction (when viewed from the distal 902 direction looking towards the proximal 901 direction). In one aspect, the servo motor associated with instrument input 940*b* is commanded to discontinue soft lock state behavior. In lieu of soft lock state behavior, in which the servo motor is generally commanded to maintain the drive shaft reference state position of the servo motor, the servo motor is instead commanded to apply a torque to resist, but not defeat, the rotation of instrument input 940*b* resulting from the medical person's actuation of lever 910. In one aspect, the purpose of this behavior is to provide a dampening effect to slow down the rate at which instrument input 940*b* is rotated. Because the rotation of instrument input 940*b* is operatively coupled to the opening of the end effector jaws of instrument 900, the ultimate effect of the slowing down the rotation of instrument input 940*b* is to slow down the opening of end effector jaws of instrument 900 when lever 910 is actuated.

Second Example

Figure 10A:
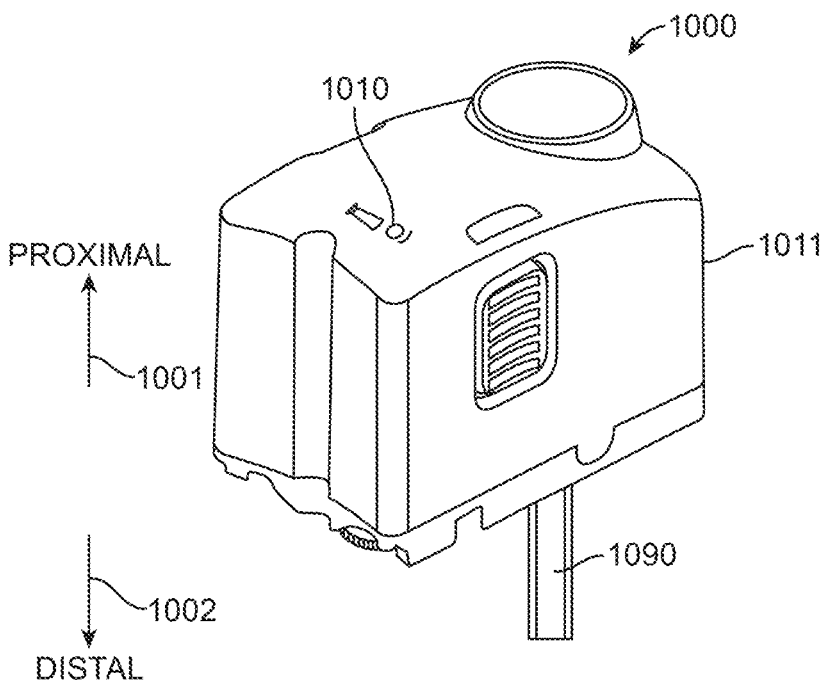
FIG. 10A is a perspective view of a proximal control portion of a surgical instrument.
Figure 10B:
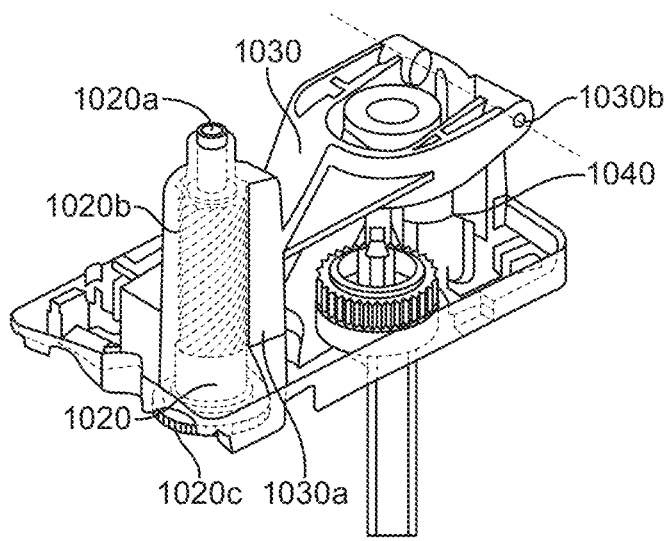
FIG. 10B is a perspective view of a proximal portion of a surgical instrument with its exterior cover removed.
Figure 10C:
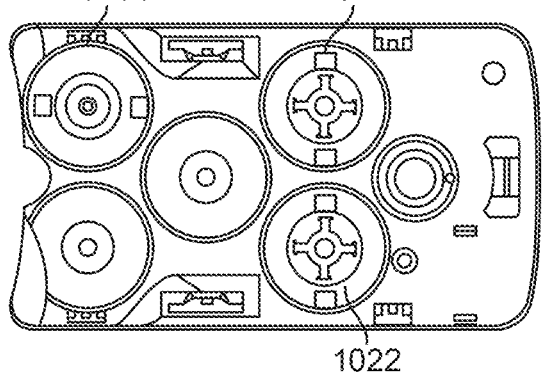
FIG. 10C is a proximal control portion of a surgical instrument viewed from the distal direction.

FIG. 10A shows a perspective view of a surgical instrument 1000. FIG. 10B shows a perspective view of instrument 1000 with instrument cover 1011 removed. FIG. 10C shows a view of instrument 1000 from a distal 1002 direction looking towards a proximal 1001 direction. In one aspect, instrument 1000 is removably coupled to the instrument carriage of an instrument manipulator, the instrument carriage housing a plurality of servo motors. Each of instrument inputs 1020*c*,1021,1022 is mechanically coupled to one of the plurality of servo motors. Accordingly, rotation of one the servo motors rotates a corresponding instrument input (i.e., one of instrument inputs 1020*c*,1021,1022). In one aspect, rotation of instrument input 1020*c* by a corresponding servo motor moves an end effector jaw of instrument 1000.

Referring to FIG. 10B, rotating instrument input 1020*c* rotates input shaft 1020. Input shaft 1020 includes geared surface 1020*b*, which engages complimentary gear surface 1030*a* of pivoting member 1030. When input shaft 1020 rotates, pivoting member 1030 rotates about axis 1030*b*. Pivoting member 1030 is coupled to elongate member 1040, which is coupled to an end effector of instrument 1000. Translation of the elongate member 1040 in a proximal 1001 direction moves a jaw of the end effector in a closing direction, and translation of the elongate member 1040 in a distal 1002 direction moves the jaw of the end effector in an opening direction. Instrument inputs 1021 and 1022 are configured to rotate instrument shaft 1090 about an instrument shaft longitudinal axis.

In one aspect, an instrument manipulator on which instrument 1000 is installed is in a soft lock state and not under the active control of a surgeon or other medical person. A reference state for the servo motors of the instrument carriage is determined, including the drive shaft rotational position of each servo motor (the drive shaft reference state position) and the torque being applied by each servo motor (the reference state torque) to maintain its respective drive shaft reference state position.

Referring to FIG. 10A, in one aspect, a medical person located at the patient side desires to open the end effector jaw of instrument 1000 from the patient side. The medical person inserts a hex wrench through opening 1010 of instrument cover 1011. The hex wrench is sized to interface with socket head feature 1020*a* (at FIG. 10B) of input shaft 1020. Once the hex wrench is properly inserted into socket head feature 1020*a*, rotating the hex wrench in a counterclockwise direction (when viewed from the proximal 1001 direction looking towards the distal 1002 direction) will apply a rotational force to input shaft 1020, which in turn rotates instrument input 1020*c*.

In one aspect, instrument 1000 is coupled to the instrument carriage portion of an instrument manipulator. A medical person applies a rotational force to instrument input 1020*c*, which in turn applies a rotational force to a servo motor mechanically coupled to instrument input 1020*c*. A controller of the instrument manipulator detects that the servo motor corresponding to instrument input 1020*c* is applying elevated torque levels to maintain its reference state motor position. The controller further detects that the drive shaft rotational position of the servo motor corresponding to at least one of instrument input 1021 (instrument shaft roll) and instrument input 1022 (instrument shaft roll) is unchanged from its drive shaft reference state position, and that the torque applied by the servo motors corresponding to instrument inputs 1021 and 1022 remains their respective reference state torques. In response, the servo motor associated with instrument input 1020*c* is commanded to discontinue soft lock state behavior. In one aspect, power to the servo motor is cut off. Accordingly, the external force applied by the medical person using the hex wrench overcomes any passive resistance of the powered-off servo motor and successfully opens the grip mechanism of instrument 1000.

Third Example

FIG. 11A shows a perspective view of a surgical instrument 1100. FIG. 11B shows a perspective view of instrument 1100 with instrument cover 1111 shown transparently. FIG. 11C shows instrument 1100 viewed from the distal 1102 direction looking towards the proximal 1101 direction. In one aspect, instrument 1100 is removably coupled to an instrument carriage portion of an instrument manipulator, the instrument carriage housing a plurality of servo motors. Each of instrument inputs 1120*b*,1140*b*,1121,1122,1123 is mechanically coupled to one of the plurality of servo motors. Accordingly, rotation of one of the servo motors rotates a corresponding instrument input (i.e., one of instrument inputs 1120*b*,1140*b*,1121,1122,1123). Referring to FIG. 11C, in one aspect, an end effector of instrument 1100 is a two jaw end effector. Each jaw of the two jaw end effector is independently controlled by an instrument input. A first jaw is operated by instrument input 1120*b*, and a second jaw is operated by instrument input 1140*b*.

Referring to FIG. 11B-11C, rotating instrument input 1123 rolls instrument shaft 1190 of instrument 1100 about an instrument shaft longitudinal axis. Rotating instrument input 1140*b* in a first direction rotates input shaft 1140 in the first direction. This increases tension in cable segment 1131*a* and reduces tension in cable segment 1131*b*. These tensions are transferred, via one or more idler pulleys 1135, to a first jaw of the two jaw end effector located at a distal end of instrument shaft 1190, producing a movement in an opening direction for the first jaw. Rotating 1140*b* in a second direction increases tension in cable segment 1131*b* and reduces tension in cable segment 1131*a*. This accordingly produces a movement in a closing direction for the first jaw.

Similarly, with respect to instrument input 1120*b*, rotating instrument input 1120*b* in a first direction rotates input shaft 1120 in the first direction. This increases tension in cable segment 1130*a* and reduces tension in cable segment 1130*b*. These tensions are transferred, via one or more idler pulleys 1135, to a second jaw of the two jaw end effector located at the distal end of instrument shaft 1190, producing a movement in the opening direction for the second jaw. Rotating 1140*b* in a second direction increase tension in cable segment 1130*b* and reduces tension in cable segment 1130*a*. This accordingly produces a movement in a closing direction for the second jaw.

The coordinated motion of instrument input 1120*b* and instrument input 1140*b* synchronously open and close the two jaws of the instrument 1100 end effector. In one aspect, to open the jaws, instrument input 1120*b* and instrument input 1140*b* are rotated in the first direction at substantially the same rate. To close the grippers, instrument input 1120*b* and instrument input 1140*b* are rotated in the second direction at substantially the same rate.

In one aspect, instrument 1100 is removably coupled to an instrument carriage portion of an instrument manipulator, and each of instrument inputs 1120*b*,1140*b*,1021,1022,1123 is mechanically coupled to one of a plurality of servo motors housed in the instrument carriage. Accordingly, rotation of one of the servo motors rotates a corresponding instrument input (i.e., one of instrument inputs 1120*b*,1140*b*,1021,1022, 1123). In one aspect, instrument manipulator to which instrument 1100 is coupled is in a soft lock state and is not under active control by a surgeon or other medical person. A reference state for the servo motors of the instrument carriage is determined, including the drive shaft rotational position of each servo motor (the drive shaft reference state position) and the torque being applied by each servo motor (the reference state torque) to maintain its respective drive shaft reference state position.

Referring to FIG. 11A, in one aspect, a medical person located at the patient side, desires to open the end effector mechanism of instrument 1100 from the patient side. In one aspect, the medical person inserts a suitably sized hex wrench through opening 1110 of instrument cover 1111 to interface with socket head feature 1120*a* (at FIG. 11B) of input shaft 1120. Once the hex wrench is properly seated in socket head feature 1120*a*, the medical person applies a rotational force to input shaft 1120 by rotating the hex wrench in a counterclockwise direction (viewed from a proximal 1101 direction looking towards a distal 1102 direction).

A controller of the instrument manipulator detects that the servo motor is being acted upon by an external force. The external force applied by the medical person causes the servo motor to be incapable of maintaining its drive shaft reference state position without applying torque in excess of its reference state torque. In one aspect, the controller further detects that the rotational position of the servo motor corresponding to instrument input 1123 (instrument shaft roll) is unchanged from its drive shaft reference state position, and that the torque applied by the servo motor corresponding to instrument input 1123 remains its reference state torque.

In response, the controller of the instrument manipulator commands the servo motor corresponding to instrument input 1020*c* to discontinue soft lock state behavior. This permits the medical person to move the second jaw of the two jaw end effector in an opening direction. In one aspect, the controller of the instrument manipulator commands a complementary, coordinated motion of the servo motor mechanically coupled to instrument input 1140*b* at the same time or nearly the same time the medical person moves the second jaw in the opening direction. Accordingly, the controller of the instrument manipulator commands the servo motor mechanically coupled to instrument input 1140*b* to move the first jaw in an opening direction at the same time as the medical person uses a hex wrench to move the second jaw of the two-jaw end effector in an opening direction. The effect of this coordination is that the first jaw and the second jaw of the two jaw end effector open at substantially the same rate in a symmetric manner.

Fourth Example

Figure 12A:
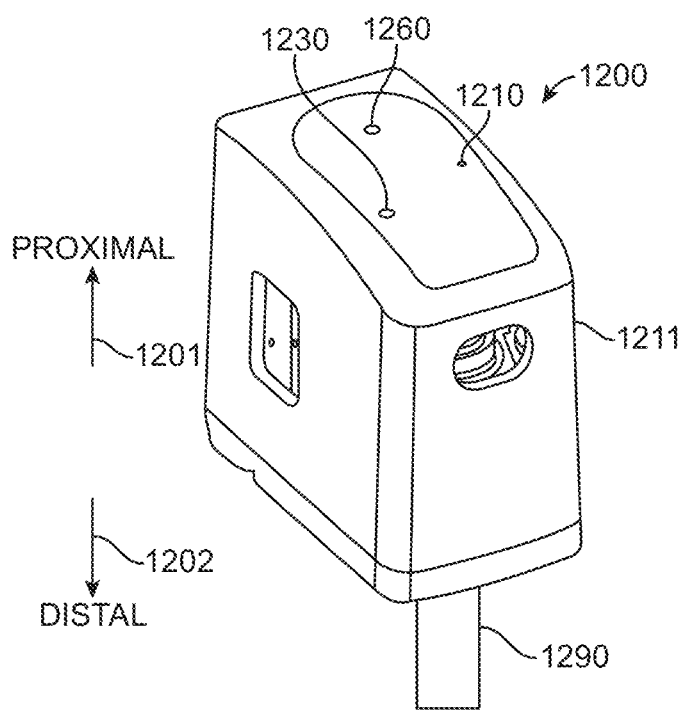
FIG. 12A is a perspective view of a proximal control portion of a surgical instrument.
Figure 12B:
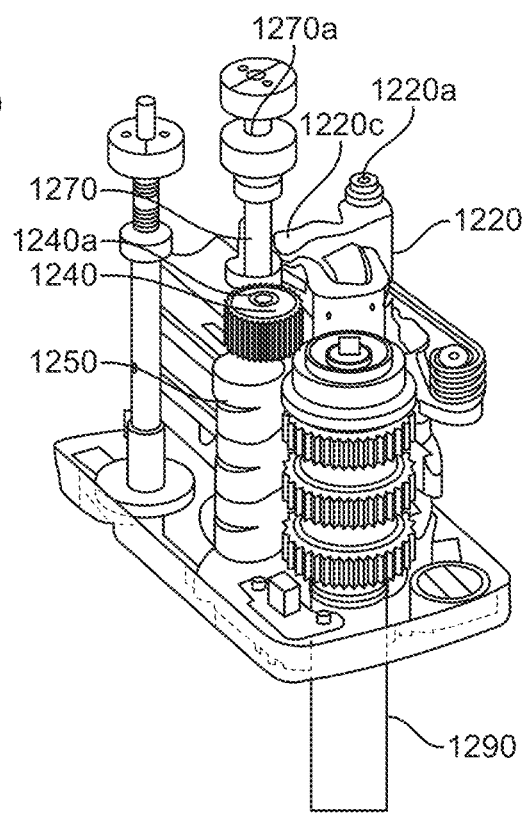
FIG. 12B is a perspective view of a proximal portion of a surgical instrument with its exterior cover removed.
Figure 12C:
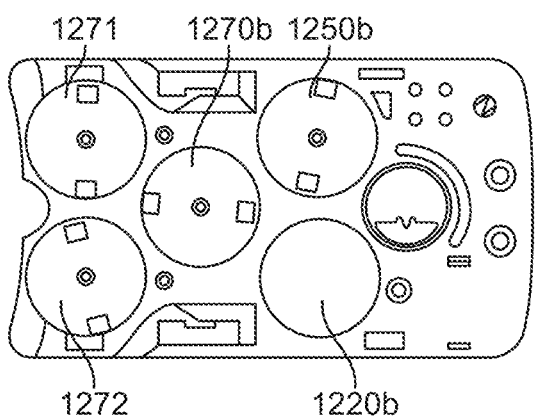
FIG. 12C is a proximal control portion of a surgical instrument viewed from the distal direction.

FIG. 12A shows a perspective view of a surgical instrument 1200. FIG. 12B shows a perspective view of instrument 1200 with instrument cover 1211 removed. FIG. 11C shows a view of instrument 1200 from the distal 1202 direction looking towards the proximal 1201 direction. In one aspect, instrument 1200 is removably coupled to the instrument carriage portion of an instrument manipulator, the instrument carriage including a plurality of servo motors. Each of instrument inputs 1220*b*,1250*b*,1270*b*,1271,1272 is mechanically coupled to one of the plurality of servo motors. Accordingly, rotation of a servo motor rotates a corresponding instrument input (i.e., one of instrument inputs 1220*b*, 1250*b*,1270*b*,1271,1272).

In one aspect, the end effector of instrument 1200 includes three mechanical degrees of freedom. A first mechanical degree of freedom is a low force jaw opening and closing mechanism that is operatively coupled to instrument input 1270*b*. A second mechanical degree of freedom and a third mechanical degree of freedom of the end effector are operatively coupled to the complementary operation of instrument inputs 1220*b* and 1250*b*. In one example, the second mechanical degree of freedom is a high force jaw closing mechanism, and the third mechanical degree of freedom enables stapler firing and tissue transecting.

In one aspect, instrument input 1220*b* operates a switching mechanism, whose rotational position determines which of a plurality of mechanical degrees of freedom is operatively coupled to the rotation of instrument input 1250*b*. Rotating instrument input 1220*b* to a first position operatively couples instrument input 1250*b* to a mechanical degree of freedom that provides high force jaw closing of the end effector located at the distal end of instrument shaft 1290. This high-force closing mechanism is complementary to the low force jaw grip opening and closing mechanism operatively coupled to instrument input 1270*b*. Rotating instrument input 1220*b* to a second position operatively couples instrument input 1250*b* to a mechanical degree of freedom that provides stapler firing and tissue transecting functionality at the end effector of instrument 1200. Rotating instrument input 1220b to a third position operatively couples instrument input 1250b to a mechanical degree of freedom that provides for rotation of instrument shaft 1290 about a shaft longitudinal axis.

In one aspect, instrument 1200 is removably coupled to the instrument carriage portion of an instrument manipulator, and each of instrument inputs 1220b,1250b,1270b,1271, 1272 is mechanically coupled to one of a plurality servo motors. In one aspect, the instrument manipulator on which instrument 1200 is installed is in a soft lock state and is not under the active control of a surgeon or other medical person. A reference state for the servo motors of the instrument carriage is determined, including the drive shaft rotational position of each servo motor (the drive shaft reference state position) and the torque being applied by each servo motor to maintain its respective drive shaft reference state position (the reference state torque).

Referring to FIG. 12A, in one aspect, a medical person located at the patient side desires to opens the end effector mechanism of instrument 1200 from the patient side by inserting a hex wrench through opening 1210 of instrument cover 1211. The hex wrench is sized to interface with socket head feature 1220a of input shaft 1220. Once the hex wrench is properly seated in socket head feature 1220a, the medical person can rotate the hex wrench in a counterclockwise direction (viewed from the proximal 1201 direction looking towards the distal 1202 direction) to apply a rotational force to input shaft 1220.

In one aspect, a controller of the instrument manipulator detects the force applied by the medical person in the form of a force acting on the servo motor associated with instrument input 1220b. The external force applied by the medical person causes the servo motor to be incapable of maintaining its drive shaft reference state position without applying torque in excess of its reference state torque. The controller further detects that the rotational position of the servo motor corresponding to instrument input 1250b is unchanged from its drive shaft reference state position, and that the torque applied by the servo motor corresponding to instrument input 1250b remains its reference state torque. In one aspect, the controller of the instrument manipulator responds to these conditions by commanding three servo motors to discontinue soft lock state behavior: the servo motor mechanically coupled to instrument input 1220b; the servo motor mechanically coupled to instrument input 1250b; and the servo motor mechanically coupled to instrument input 1270b. In one aspect, power is cut off to all three servo motors.

In one aspect, the medical person uses the hex wrench inserted into socket head feature 1220a to rotate input shaft 1220 into the first position. Using the hex wrench, the medical person is able to apply an external force to instrument input 1220b, which is transmitted to the servo motor mechanically coupled to instrument input 1220b. In one aspect, the servo motor mechanically coupled to instrument input 1220b had earlier been commanded to discontinue soft lock state behavior. Further, power was cut off to the servo motor. Accordingly, the external force applied by the medical person using the hex wrench can overcome any passive resistance of the powered-off servo motor. When input shaft 1220 is in the first position, instrument input 1250b is operatively coupled to a mechanical degree of freedom that provides high force closing of an end effector at the distal end of instrument shaft 1290.

In one aspect, a protective element 1220c is configured to occlude opening 1230, and prevent access to socket head feature 1240a. Use of a hex wrench to rotate socket head feature 1220a into the first position moves the protective element 1220c and allows access by the hex wrench to socket head feature 1240a. This permits the medical person to inserts the hex wrench through opening 1230 to engage with socket head feature 1240a. Socket head feature 1240a is operatively coupled to input shaft 1250 via gear 1240. Input shaft 1250 is further coupled to instrument input 1250b, which is mechanically coupled to a corresponding servo motor. In one aspect, the servo motor mechanically coupled to instrument input 1250b had earlier been commanded to discontinue soft lock state behavior. Further, power was cut off to the servo motor. Accordingly, the external force applied by the medical person using the hex wrench can overcome any passive resistance of the powered-off servo motor mechanically coupled to instrument input 1250b. Thus, the medical person is able to use the hex wrench to rotate input shaft 1250 and corresponding instrument input 1250b. In one aspect, rotation of the hex wrench inserted in socket head feature 1240a releases a high force jaw closing mechanism the instrument 1200 end effector.

In one aspect, the medical person removes the hex wrench from socket head feature 1240a and out of opening 1230, and inserts the hex wrench through opening 1260 to engage with socket head feature 1270a. Socket head feature 1270a is coupled to input shaft 1270, which is in turn coupled to instrument input 1270b. Instrument input 1270b is coupled to a low force end effector jaw opening and closing mechanical degree of freedom. In one aspect, the servo motor mechanically coupled to instrument input 1270b had earlier been commanded to discontinue soft lock state behavior. Further, power was cut off to the servo motor. Accordingly, an external force applied by the medical person using the hex wrench can overcome any passive resistance of the powered-off servo motor mechanically coupled to instrument input 1250b. In one aspect, the medical person uses a hex wrench engaged with socket head feature 1270a to rotate instrument shaft 1270, which in turn actuates the low force end effector jaw opening and closing degree of freedom to open the end effector.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

We claim:

1. A system comprising:
   a first actuator;
   a second actuator; and
   a controller;
   wherein the controller is configured to:
   command the first actuator to maintain a first mechanical degree of freedom of an instrument at a first position;
   command the second actuator to maintain a second mechanical degree of freedom of the instrument at a second position;
   detect, at the first actuator while the first actuator is maintaining the first mechanical degree of freedom at the first position, a first manual actuation of the first actuator that exceeds a first threshold;

detect, at the second actuator while the second actuator is maintaining the second mechanical degree of freedom at the second position, a second manual actuation of the second actuator that does not exceed a second threshold; and in response to detecting that the first manual actuation exceeds the first threshold and detecting that the second manual actuation does not exceed the second threshold, terminate the command to the first actuator to maintain the first mechanical degree of freedom at the first position.

2. The system of claim 1, wherein the first manual actuation is caused by user actuation of a mechanical feature of the instrument.

3. The system of claim 2, wherein the mechanical feature is a lever or a socket head.

4. The system of claim 2, wherein the mechanical feature is coupled to the first mechanical degree of freedom by one or more of a pullwire, a tendon, a pulley, or a gear.

5. The system of claim 1, wherein to detect the first manual actuation of the first actuator that exceeds the first threshold, the controller is configured to determine an electrical current supplied to the first actuator.

6. The system of claim 1, wherein to terminate the command to the first actuator to maintain the first mechanical degree of freedom at the first position, the controller is configured to permit a movement of the first mechanical degree of freedom from the first position to a third position.

7. The system of claim 1, wherein to terminate the command to the first actuator to maintain the first mechanical degree of freedom at the first position, the controller is configured to discontinue a supply of electrical power to the first actuator.

8. The system of claim 1, wherein to terminate the command to the first actuator to maintain the first mechanical degree of freedom at the first position, the controller is configured to command the first actuator to oppose but not prevent a movement of the first mechanical degree of freedom resulting from the first manual actuation.

9. The system of claim 1, wherein the controller is further configured to present a notification that a manual actuation of the instrument is being attempted.

10. The system of claim 1, wherein the controller is further configured to terminate the command to the second actuator to maintain the second mechanical degree of freedom at the second position.

11. A method comprising:
commanding a first actuator to maintain a first mechanical degree of freedom of an instrument at a first position;
commanding a second actuator to maintain a second mechanical degree of freedom of the instrument at a second position;
detecting, at the first actuator while the first actuator is maintaining the first mechanical degree of freedom at the first position, a first manual actuation of the first actuator that exceeds a first threshold;
detecting, at the second actuator while the second actuator is maintaining the second mechanical degree of freedom at the second position, a second manual actuation of the second actuator that does not exceed a second threshold; and
in response to the detecting that the first manual actuation exceeds the first threshold and detecting that the second manual actuation does not exceed the second threshold, terminating the commanding of the first actuator to maintain the first mechanical degree of freedom at the first position.

12. The method of claim 11, wherein the first manual actuation is caused by user actuation of a mechanical feature of the instrument.

13. The method of claim 12, wherein the mechanical feature is a lever or a socket head.

14. The method of claim 12, wherein the mechanical feature is coupled to the first mechanical degree of freedom by one or more of a pullwire, a tendon, a pulley, or a gear.

15. The method of claim 11, wherein detecting the first manual actuation of the first actuator that exceeds the first threshold comprises determining an electrical current supplied to the first actuator.

16. The method of claim 11, wherein terminating the commanding of the first actuator to maintain the first mechanical degree of freedom at the first position comprises permitting a movement of the first mechanical degree of freedom from the first position to a third position.

17. The method of claim 11, wherein terminating the commanding of the first actuator to maintain the first mechanical degree of freedom at the first position comprises discontinuing a supply of electrical power to the first actuator.

18. The method of claim 11, wherein terminating the commanding of the first actuator to maintain the first mechanical degree of freedom at the first position comprises commanding the first actuator to oppose but not prevent a movement of the first mechanical degree of freedom resulting from the first manual actuation.

19. The method of claim 11, further comprising presenting a notification that a manual actuation of the instrument is being attempted.

20. The method of claim 11, further comprising terminating the commanding to the second actuator to maintain the second mechanical degree of freedom at the second position.

* * * * *

UNITED STATES PATENT AND TRADEMARK OFFICE
CERTIFICATE OF CORRECTION

Page 1 of 1

PATENT NO. : 11,648,072 B2
APPLICATION NO. : 17/065483
DATED : May 16, 2023
INVENTOR(S) : Hsien-Hsin Liao et al.

It is certified that error appears in the above-identified patent and that said Letters Patent is hereby corrected as shown below:

On the Title Page

(63) Related U.S. Application Data:
Please delete "Continuation of application No. 15/580,629, filed as application No. PCT/US2016/036849 on Jun. 10, 2016, now Pat. No. 10,806,530." and insert --Continuation of application No. 15/580,629, filed on Dec. 7, 2017, now Pat. No. 10,806,530, which is a 371 of application No. PCT/US2016/036849, filed on Jun. 10, 2016.--.

Signed and Sealed this
First Day of April, 2025

Coke Morgan Stewart
*Acting Director of the United States Patent and Trademark Office*